US010857517B2

(12) United States Patent
Zhang et al.

(10) Patent No.: US 10,857,517 B2
(45) Date of Patent: Dec. 8, 2020

(54) POROUS CHIRAL MATERIALS AND USES THEREOF

(71) Applicants: NANKAI UNIVERSITY, Tianjin (CN); UNIVERSITY OF LIMERICK, Limerick (IE)

(72) Inventors: Shi-Yuan Zhang, Limerick (IE); Cheng-Xiong Yang, Tianjin (CN); Wei Shi, Tianji (CN); Xiu-Ping Yan, Tianjin (CN); Peng Cheng, Tianjin (CN); Michael J. Zaworotko, Limerick (IE)

(73) Assignees: NANKAI UNIVERSITY, Tianjin (CN); UNIVERSITY OF LIMERICK, Limerick (IE)

( * ) Notice: Subject to any disclaimer, the term of this patent is extended or adjusted under 35 U.S.C. 154(b) by 0 days.

(21) Appl. No.: 16/327,784

(22) PCT Filed: Aug. 22, 2016

(86) PCT No.: PCT/CN2016/096168
§ 371 (c)(1),
(2) Date: Feb. 22, 2019

(87) PCT Pub. No.: WO2018/035660
PCT Pub. Date: Mar. 1, 2018

(65) Prior Publication Data
US 2020/0009531 A1 Jan. 9, 2020

(51) Int. Cl.
| | | |
|---|---|---|
| B01J 20/29 | (2006.01) |
| B01D 15/38 | (2006.01) |
| B01J 20/22 | (2006.01) |
| B01J 20/282 | (2006.01) |
| B01J 20/32 | (2006.01) |
| C07B 57/00 | (2006.01) |
| C07C 29/76 | (2006.01) |
| C07C 59/50 | (2006.01) |
| C07C 59/56 | (2006.01) |
| C07C 253/34 | (2006.01) |
| C07F 15/06 | (2006.01) |

(52) U.S. Cl.
CPC .......... *B01J 20/29* (2013.01); *B01D 15/3833* (2013.01); *B01J 20/226* (2013.01); *B01J 20/282* (2013.01); *B01J 20/3268* (2013.01); *C07B 57/00* (2013.01); *C07C 29/76* (2013.01); *C07C 59/50* (2013.01); *C07C 59/56* (2013.01); *C07C 253/34* (2013.01); *C07F 15/065* (2013.01); *B01J 2220/86* (2013.01); *C07B 2200/07* (2013.01)

(58) Field of Classification Search
CPC ...................................................... B01J 20/29
See application file for complete search history.

(56) References Cited

PUBLICATIONS

Li "Applications of homochiral metal-organic frameworks in enantioselective adsorption and chromatography separation" Electrophoresis 2014, 35, 2733-2743.*
Dorwald F. A. Side Reactions in Organic Synthesis, 2005, Wiley: VCH, Weinheim p. IX of Preface p. 1-16.*
Zhang "Homochiral Metal-Organic Materials: Design, Synthetic and Enantioseletive Separation" Dissertation University of South Florida, 2014.*
Moghadam "Origin of Enantioselectivity in a Chiral Metal-Organic Framework: A Molecular Simulation Study" J. Phys. Chem. C 2012, 116, 20874-20881.*
Novitchi "1D Coll and Nill Chiral Polymers That Exhibit Ferromagnetic Interactions" Eur. J. Inorg. Chem. 2011, 4869-4877.*
Guo "Architectural diversity of six coordination compounds based on (S)-(+)-mandelic acid and different N-donor auxiliary ligands: syntheses, structures, and luminescent properties" Journal of Coordination Chemistry, 2015 vol. 68, No. 23, 4224-4241.*
PCT International Search Report and Written Opinion for International Application No. PCT/CN2016/096168, dated May 17, 2017, 12 pages.
Dybtsev et al., "Modular, Homochiral, Porous Coordination Polymers: Rational Design, Enantioselective Guest Exchange Sorption and Ab Initio Calculations of Host—Guest Interactions," First published Aug. 20, 2010, 4 pages.
Gu et al., "Enantioselective Adsorption in Homochiral Metal-Organic Frameworks: The Pore Size Influence," Royal Society of Chemistry, Chemical Communications, 2015, 51, 8998, 5 pages.
Xie et al., "A 3-D open-framework material with intrinsic chiral topology used as a stationary phase in gas chromatography," Original paper first online Jan. 30, 2013, 2 pages.
Xie et al., "A 3-D open-framework material with intrinsic chiral topology used as a stationary phase in gas chromatography," Analytical and Bioanalytical Chemistry Electronic Supplementary Material, Figures, 5 pages.
Zhang et al., "Structural Insight into Guest Binding Sites in a Porous Homochiral Metal-Organic Material," Journal of the American Chemical Society, Department of Chemical & Environmental Science, Materials and Surface Science Institute, University of Limerick, Department of Chemistry, University of South Florida, 2015 American Chemical Society, 5 pages.
European Search Report for Application No. 16913684.3, dated Feb. 14, 2020, 9 pagea.
Zhang et al., "A pair of nonporous homochiral cobalt-based coordination polymers for enantioselective recognition and electrocatalysis," Inorganic Chemistry Communications, vol. 69, Apr. 27, 2016, 5 pages.
Lu et al., "Palladacycles with a Metal-Bonded sp3-Hybridized Carbon as Intermediates in the Synthesis of 2,2,3,4-Tetrasubstitued 2H-1-Benzopyrans and 1,2-Dihydroquinolines. Effects of Auxiliary Ligands and Substitution at a Palladium-Bonded Tertiary Carbon," Organometallics, vol. 24, No. 5, Jan. 27, 2005, 17 pages.
El-Shahawi et al., "Chromium (III) Complexes with Some Optically Active a-Hyroxy Acids," B:Chemical Sciences, vol. 48, No. 3, Mar. 1, 1993, 5 pages.

* cited by examiner

*Primary Examiner* — David K O'Dell
(74) *Attorney, Agent, or Firm* — Hoffman Warnick LLC

(57) ABSTRACT

A porous chiral material of formula $[M(L)_{1.5}(A)]^+X^-$ wherein M is a metal ion; L is a nitrogen-containing bidentate ligand; A is the anion of mandelic acid or a related acid; and $X^-$ is an anion.

8 Claims, 10 Drawing Sheets

POROUS CHIRAL MATERIALS AND USES THEREOF

The present invention relates to novel chiral metal-organic materials and to methods and uses relating thereto.

In particular the invention relates to the use of such materials for the separation of enantiomers, the structural characterisation of molecules and as chiral crystalline sponges.

Enantiomerically pure materials are produced by nature but replicating this by synthetic routes remains challenging and many synthetic products contain a mixture of enantiomers. Due to their identical physical and chemical properties, the separation and characterisation of enantiomers is very difficult. Whilst crystallisation can afford enantiomerically pure compounds which can be characterised using X-ray diffraction techniques, this can be impossible when only very small amounts of a compound are available. This is often the case in the pharmaceutical field when developing new chemical entities, or when isolating compounds from natural products.

It can be possible to separate enantiomers using chiral chromatography in which a column is provided with a chiral stationary phase (CSP) that selectively binds more strongly to one enantiomer. However such columns are effective only for a limited range of analytes and an enantiopure reference standard is needed to identify each enantiomer.

In addition many current commercially available CSPs are very expensive to manufacture and degrade easily.

Structural determination using trace amounts of materials has been achieved previously using "crystalline sponges". These porous materials can accommodate guest molecules which can be examined by crystallisation of the host material. However, although chiral porous materials are known, they have not been shown to be able to function as crystalline sponges.

It is an aim of the present invention to provide novel materials and improved methods for the separation and characterisation of enantiomers.

BRIEF DESCRIPTION OF TH DRAWINGS

Figure 1:
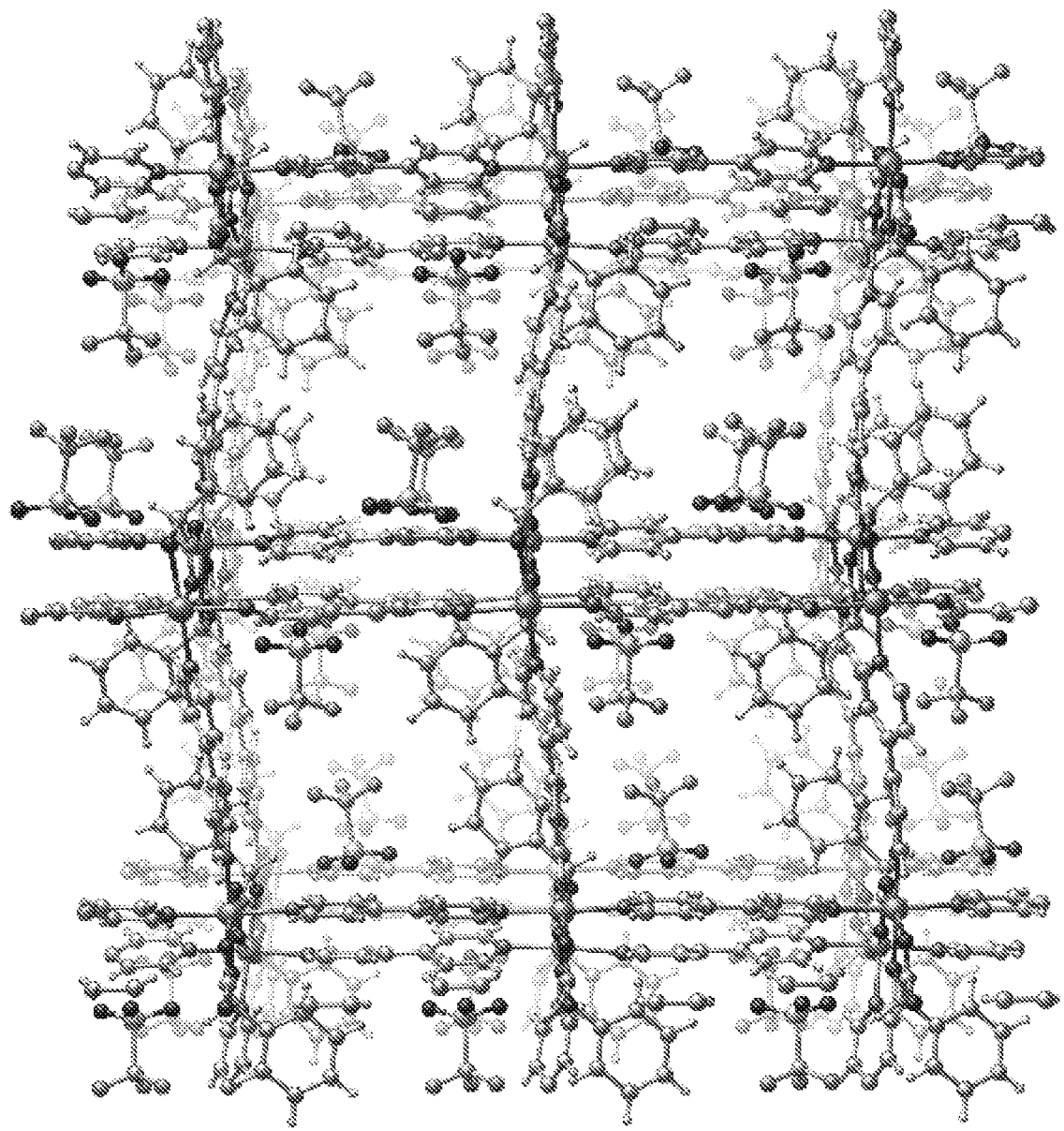
FIG. 1 shows the crystal structure of [Co(biyp)$_{1.5}$(1S)].OTf⁻.

According to a first aspect of the present invention there is provided a porous chiral material of formula [M(L)$_{1.5}$(A)]⁺X⁻ wherein M is a metal ion; L is a nitrogen-containing bidentate ligand; A is the anion of mandelic acid or a related acid; and X⁻ is an anion.

The porous chiral material suitably comprises a metal-organic material. The acid A is a component of the framework of the metal-organic material. X is suitably an anion that balances the charge of the metal-organic material.

M is a transition metal ion.

Preferably M is a metal ion selected from cobalt, chromium, iron, nickel, manganese, calcium, magnesium, cadmium, copper and zinc.

Suitably the metal is present in the +2 or +3 oxidation state. Preferably it is present in the +2 oxidation state.

Preferably M is a transition metal. Suitably M is a first row transition metal.

Preferably M is selected from cobalt, cadmium, copper and zinc.

More preferably M is selected from nickel and cobalt.

Most preferably M is cobalt.

L is a nitrogen-containing bidentate ligand. Suitably L is a nitrogen ligand comprising at least two donor atoms which are nitrogen atoms. Suitably the at least two nitrogen atoms each comprise a lone pair of electrons suitable for binding to a metal species. Therefore the nitrogen ligands are suitably two-connected nitrogen ligands. By "two-connected" we mean the nitrogen ligand is capable of binding to two different metal species (M) in the porous chiral material. In preferred embodiments the lone pairs of electrons on the two nitrogen atoms are in orbitals orientated away from each other at an angle capable of forming a lattice, for example an angle greater than 90°, for example an angle of approximately 120° or an angle of approximately 180°.

Suitably L is a two-connected nitrogen ligand. Preferred two-connected nitrogen ligands comprise at least one nitrogen-containing heterocycle. In some embodiments the two-connected nitrogen ligand may be a nitrogen-containing heterocycle comprising two nitrogen atoms each having a lone pair of electrons.

In some embodiments the two-connected nitrogen ligand comprises two nitrogen-containing heterocycles. The two nitrogen-containing heterocycles may be linked together by a bond. One such preferred two-connected nitrogen ligand is 4,4'-bipyridine.

Alternatively, the two nitrogen-containing heterocycles may be linked together by a spacer group, for example acetylene or ethylene. Some preferred two-connected nitrogen ligands include 4,4'-bipyridylacetylene and 1,2-bis(4-pyridyl)ethane. Suitably L is a two-connected nitrogen ligand having the formula (L2N):

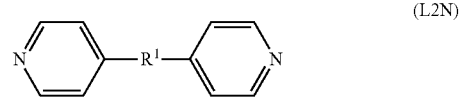

(L2N)

wherein R¹ is an optionally substituted linker group.

R¹ may be a heteroatom, a group of connected heteroatoms or a group comprising heteroatoms. For example R¹ may be a —N=N— group.

R¹ may be a hydrocarbyl group. The hydrocarbyl group may comprise a cyclic group. The hydrocarbyl group may comprise an aromatic cyclic group. The hydrocarbyl group may comprise a heterocyclic group.

As used herein, the term "hydrocarbyl" is used in its ordinary sense, which is well-known to those skilled in the art. Specifically, it refers to a group having predominantly hydrocarbon character. Examples of hydrocarbyl groups include:

(i) hydrocarbon groups, that is, aliphatic (which may be saturated or unsaturated, linear or branched, e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(ii) substituted hydrocarbon groups, that is, substituents containing non-hydrocarbon groups which, in the context of this invention, do not alter the predominantly hydrocarbon nature of the substituent (e.g., halo (especially chloro and fluoro), hydroxy, alkoxy, keto, acyl, cyano, mercapto, alkylmercapto, amino, alkylamino, nitro, nitroso, and sulphoxy);

(iii) hetero substituents, that is, substituents which, while having a predominantly hydrocarbon character, in the context of this invention, contain other than carbon in a ring or chain otherwise composed of carbon atoms. Heteroatoms include sulphur, oxygen, nitrogen, and encompass substituents as pyridyl, furyl, thienyl and imidazolyl.

Suitable two-connected nitrogen ligands may be selected from 4,4'-bipyridylacetylene and compounds (LA) to (LFF):

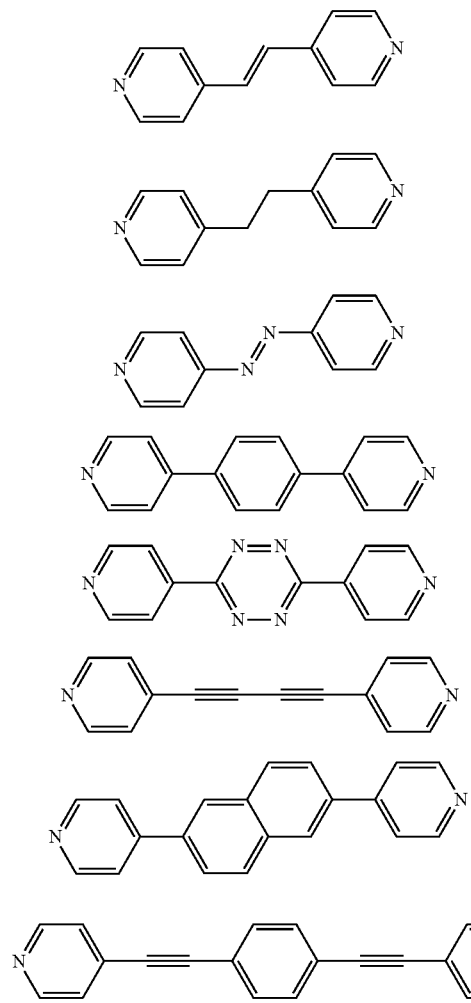

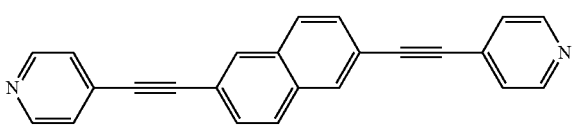

(LI)

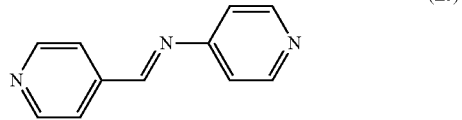

(LJ)

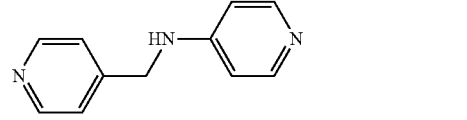

(LK)

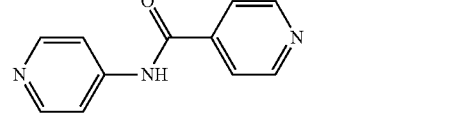

(LL)

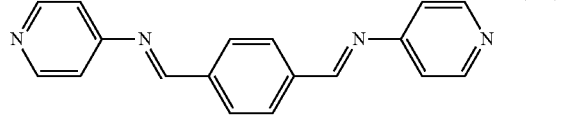

(LM)

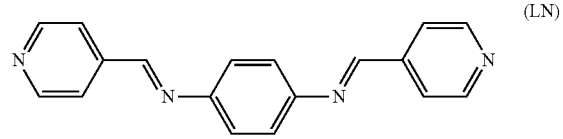

(LN)

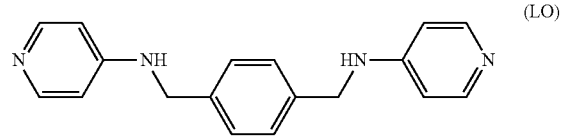

(LO)

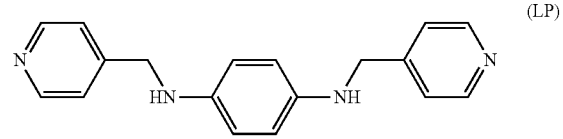

(LP)

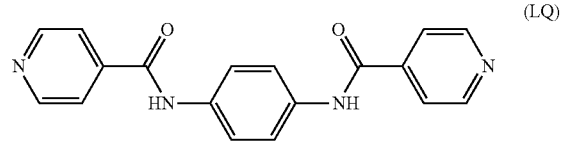

(LQ)

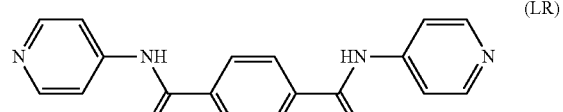

(LR)

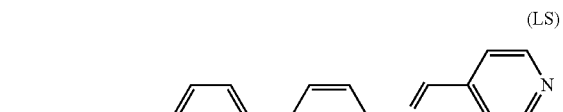

(LS)

(LT) 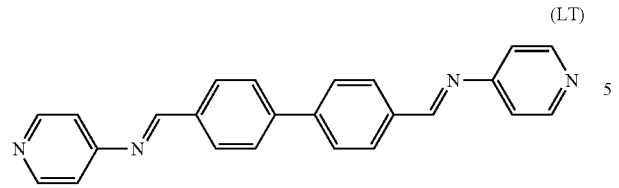
(LAA) 
(LU) 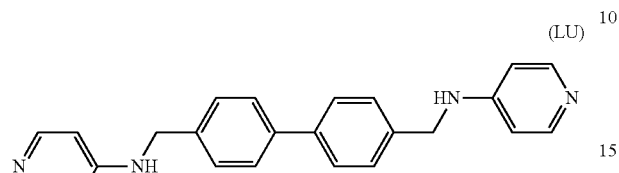
(LBB) 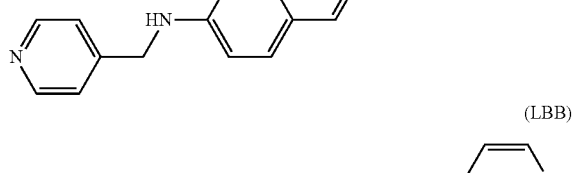
(LV) 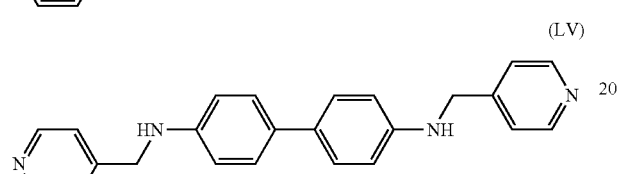
(LCC) 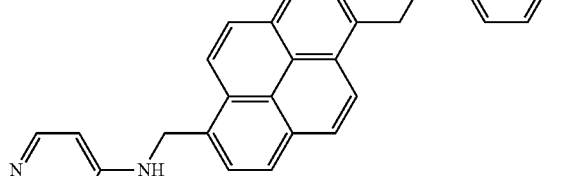
(LW) 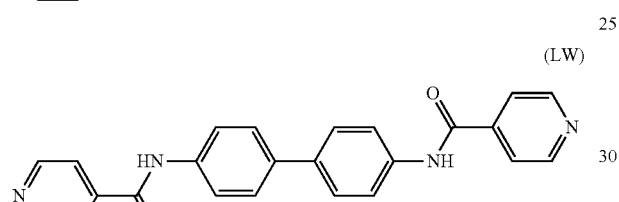
(LX) 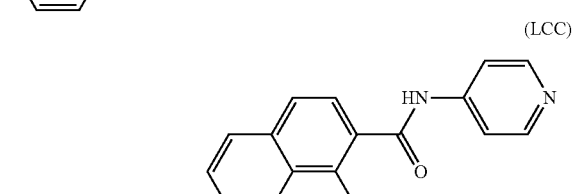
(LDD) 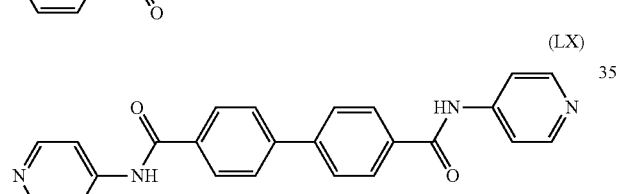
(LY) 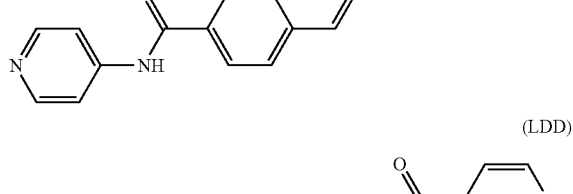
(LEE) 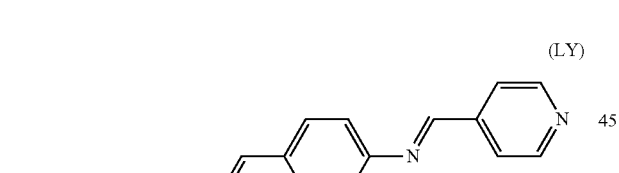
(LZ) 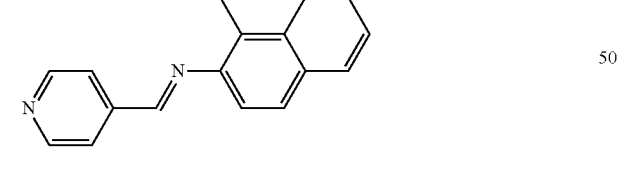
(LFF) 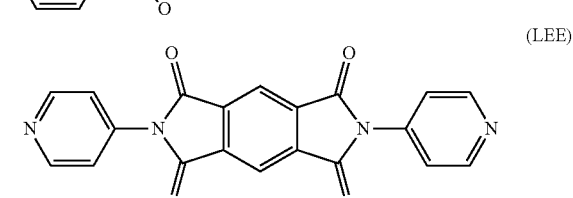
Suitably L is a two-connected nitrogen ligand selected from 4,4'-bipyridine, 1,2-bis(4-pyridyl)ethane and 4,4'-bipyridylacetylene.

Preferably L is 1,2-bis(4-pyridyl)ethane or 4,4'-bipyridine.

Most preferably L is 4,4'-bipyridine.

Suitably ligands L in the porous chiral material are the same.

A is the anion of mandelic acid or a related acid. By a related acid we mean to refer to the anion of a substituted mandelic acid or an analogous compound including the same functional groups.

Suitably the anion has the formula (I):

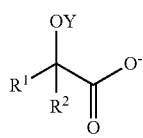

Formula (I)

wherein $R^1$ is an optionally substituted hydrocarbyl group, $R^2$ is hydrogen or an optionally substituted hydrocarbyl group and Y is hydrogen or an optionally substituted hydrocarbyl group. Suitable hydrocarbyl groups are as previously defined herein.

Suitably Y is hydrogen or an optionally substituted alkyl group. Preferably Y is hydrogen or a $C_1$ to $C_4$ alkyl group. More preferably Y is hydrogen or methyl. Most preferably Y is hydrogen.

$R^1$ may be an optionally substituted alkyl, cycloalkyl or aryl group. Preferably $R^1$ is an optionally substituted aryl group. Preferably $R^1$ is an optionally substituted phenyl, bi-phenyl or naphthyl group. Suitable substituents include alkyl (especially $C_1$ to $C_4$ alkyl), fluoroalkyl (especially $C_1$ to $C_4$ fluoroalkyl) and halo. Preferred substituents include fluoro, chloro, bromo, methyl, trifluoromethyl, methylenedioxy and isobutyl.

$R^2$ is hydrogen or an optionally substituted hydrocarbyl group. Preferably $R^2$ is hydrogen or an optionally substituted alkyl or aryl group.

Suitably $R^2$ is hydrogen, a $C_1$ to $C_6$ alkyl or cycloalkyl group, or phenyl. Preferably $R^2$ is selected from hydrogen, methyl, ethyl, isopropyl, cyclopentyl, cyclohexyl and phenyl.

Suitable mandelic acid related compounds which may be used to provide anion A in the porous chiral materials of the present invention include (R)-(−)-mandelic acid, (R)-2-chloromandelic acid, (S)-(−)-mandelic acid, (S)-2-chloromandelic acid, (R)-3-chloromandelic acid, (R)-4-chloromandelic acid, (S)-3-chloromandelic acid, (S)-4-chloromandelic acid, (R)-2-fluoromandelic acid, (R)-3-fluoromandelic acid, (S)-2-fluoromandelic acid, (S)-3-fluoromandelic acid, (R)-4-fluoromandelic acid, (R)-2-bromomandelic acid, (S)-4-fluoromandelic acid, (S)-2-bromomandelic acid, (R)-3-bromomandelic acid, (R)-4-bromomandelic acid, (S)-3-bromomandelic acid, (S)-4-bromomandelic acid, (R)-2-methylmandelic acid, (R)-3-methylmandelic acid, (S)-2-methylmandelic acid, (S)-3-methylmandelic acid, (R)-4-methylmandelic acid, (R)-2-trifluoromethylmandelic acid, (S)-4-methylmandelic acid, (S)-2-trifluoromethylmandelic acid, (R)-3-trifluoromethylmandelic acid, (S)-3-trifluoromethylmandelic acid, (R)-4-trifluoromethylmandelic acid, (S)-4-trifluoromethylmandelic acid, (R)-3,4-(methylenedioxy)mandelic acid, (S)-3,4-(methylenedioxy)mandelic acid, (R)-(−)-a-methoxyphenylacetic acid, (S)-(−)-a-methoxyphenylacetic acid, (R)-(+)-2-hydroxy-2-phenylpropionic acid, (S)-(+)-2-hydroxy-2-phenylpropionic acid, (R)-2-hydroxy-2-phenylbutyric acid, (S)-2-hydroxy-2-phenylbutyric acid, (R)-2-hydroxy-2-(4-isobutylphenyl)propanoic acid, (S)-2-hydroxy-2-(4-isobutylphenyl)propanoic acid, (R)-cyclopentyl(hydroxy)phenylacetic acid, (S)-cyclopentyl(hydroxy)phenylacetic acid, (R)-cyclohexyl(hydroxy)phenylacetic acid, (S)-cyclohexyl(hydroxy)phenylacetic acid, (R)-2-(4-chlorophenyl)-2-hydroxy-3-methylbutanoic acid, (S)-2-(4-chlorophenyl)-2-hydroxy-3-methylbutanoic acid, (R)-2-[1, 1-biphenyl]-4-yl-2-hydroxputanoic acid, (S)-2-[1, 1-biphenyl]-4-yl-2-hydroxynutanoic acid, (R)-2-[1, 1-biphenyl]-4-yl-2-hydroxypropanoic acid, (S)-2-[1, 1-biphenyl]-4-yl-2-hydroxpropanoic acid, (R)-[1, 1-biphenyl]-4-yl (hydroxy)phenylacetic acid, (S)-[1, 1-biphenyl]-4-yl (hydroxy)phenylacetic acid, (R)-(+)-alpha-methoxyphenylacetic acid, (S)-(+)-alpha-methoxyphenylacetic acid, (R)-2-methoxy-2-phenylpropanoic acid, (S)-2-methoxy-2-phenylpropanoic acid, (R)-2-hydroxy-2-(naphthalene-2-yl)acetic acid, (S)-2-hydroxy-2-(naphthalene-2-yl)acetic acid, (2R)-3,3,3-trifluoro-2-methoxy-2-phenylpropanoic acid, (2 S)-3,3,3-trifluoro-2-methoxy-2-phenylpropanoic acid, (R)-2-hydroxy-2-(naphthalen-1-yl)acetic acid, (S)-2-hydroxy-2-(naphthalene-1-yl)acetic acid, (R)-2-hydroxy-2-(4-methoxyphenyl)acetic acid and (S)-2-hydroxy-(4-methoxyphenyl)acetic acid.

Suitably A is an anion of formula (II):

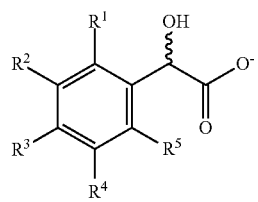

(II)

wherein the stereocentre may be (R) or (S) and $R^1$, $R^2$, $R^3$, $R^4$ and $R^5$ is each independently selected from hydrogen, hydroxy, amino, halo (especially chloro or bromo), alkyl (especially $C_1$ to $C_4$ alkyl), fluoroalkyl (especially $C_1$ to $C_4$ fluoroalkyl), sulfo, mercapto, alkoxy (especially $C_1$ to $C_4$ alkoxy), nitro, acyl and nitrilo.

Preferably each of $R^1$, $R^2$, $R^3$, $R^4$ and $R^5$ is selected from hydrogen, halo and alkyl.

More preferably each of $R^1$, $R^2$, $R^3$, $R^4$ and $R^5$ is selected from hydrogen, chloro and methyl. Preferably the mandelate ion is unsubstituted or monosubstituted on the phenyl ring.

Preferably $R^1$ is hydrogen or chloro.
Preferably $R^2$ is hydrogen or chloro.
Preferably $R^3$ is hydrogen, chloro or methyl.
Preferably $R^4$ is hydrogen or chloro.
Preferably $R^5$ is hydrogen or chloro.

Preferably A is selected from the anions of (S)-mandelic acid; (R)-2 chloromandelic acid; (R)-3-chloromandelic acid; (R)-4-chloromandelic acid and (R)-4-methyl mandelic acid.

Most preferably A is the anion of mandelic acid. It may be is the anion of (S)-mandelic acid or of (R)-mandelic acid.

Preferably A is a chiral anion. Preferably the anion is provided as a single enantiomer. Suitably the source of anion A has an enantiomeric excess (ee) of at least 90%, preferably at least 95%, more preferably at least 99%.

Suitably substantially all of the anions present in the chiral porous material have the same absolute stereochemistry.

$X^−$ is an anion. It may be an organic anion or an inorganic anion.

Suitable inorganic anions include nitrate $NO_3^-$, tetrafluoroborate $BF_4^-$ and hexafluorophosphate $PF_6^-$.

In some preferred embodiments the anion is not nitrate.

Preferably $X^-$ is an organic anion. The anion may be an organic species with a single charged moiety or it may be part of a larger organic species with more than one charged moiety.

Preferably $X^-$ comprises a sulfonate or carboxylate anion.

Suitably $X^-$ is $RCOO^-$ or $RSO_3^-$ wherein R is an optionally substituted alkyl, alkenyl or aryl group. In some embodiments R may include one or more further $COO^-$ or $SO_3^-$ residues.

R is an optionally substituted alkyl, alkenyl or aryl group. Suitable substituents include hydroxy, amino, alkoxy, fluoro, chloro, bromo, sulfo, carboxy, mercapto, nitro and nitrile.

In some embodiments R is an alkyl or a fluroalkyl group, preferably a $C_1$ to $C_4$ alkyl or fluroalkyl group.

Most preferably R is a $CF_3$ and $X^-$ is a triflate ion, $CF_3SO_3^-$ (or $^-OTf$).

In some preferred embodiments the present invention provides a porous chiral material of formula $[M(L)_{1.5}(A)]^+$ $OTf^-$, wherein M, L and $X^-$ are as previously defined herein.

In some preferred embodiments the present invention provides a porous chiral material of formula $[Co(L)_{1.5}(A)]^+$ $X^-$, wherein L, A and $X^-$ are as previously defined herein.

In some preferred embodiments the present invention provides a porous chiral material of formula $[M(bpy)_{1.5}(A)]^+X^-$ wherein bpy is 4,4'-bipyridine and M, A and $X^-$ are as previously defined herein.

In some preferred embodiments the present invention provides a porous chiral material of formula $[Co(L)_{1.5}(A)]^+$ $OTf^-$ wherein L and A are as previously defined herein.

In some preferred embodiments the present invention provides a porous chiral material of formula $(Co(bpy)_{1.5}(A)]$ $OTf^-$ wherein A is a mandelic acid derived anion. Preferably A is selected from mandelate anion, a chloro-substituted mandelate anion and an alkyl substituted mandelate anion. Most preferably A is (S)-mandelate, i.e. the anion of (S)-mandelic acid or (R)-mandelate, i.e. the anion a (R)-mandelic acid.

The materials of the present invention are porous chiral materials.

By porous we mean that the material has cavities or channels into which other materials may flow.

By chiral we mean that the material has a defined stereochemical configuration and its mirror image would not be superimposable on it.

The porous chiral materials of the present invention may be provided in crystalline form.

Thus the present invention suitably provides a crystalline material of formula $[M(L)_{1.5}(A)]^+X^-$ wherein M, L, A and $X^-$ are as previously defined herein.

The material is suitably in the form of an extended coordination network. The structure suitably contain channels which provide porosity. The channels may accommodate guest molecules. Preferably the channels are one-dimensional.

An advantage of the porous chiral materials of the present invention is that they are stable to heat and humidity. Preferably the porous chiral materials of the present invention are stable at temperatures of up to 100° C., preferably up to 200° C., for example up to 250° C. or up to 300° C.

By stable we mean that the material retains its shape and form and does not degrade physically or chemically.

The porous chiral materials of the present invention are stable to solvent exchange, as well as being thermally and hydrolytically stable.

The materials of the present invention also are particularly advantageous because they are easy to prepare from cheap starting materials and they readily crystallise.

According to a second aspect of the present invention there is provided a method of preparing a porous chiral material of formula $[M(L)_{1.5}(A)]^+X^-$, the method comprising admixing a salt of the metal with the ligand L and the acid A.

Preferred features of the second aspect are as defined in relation to the first aspect.

Any suitable salt of the metal will be used. In preferred embodiments the method involves admixing a salt of the metal cation and the anion $X^-$, which is the anion present in the final material. However embodiments involving an initial synthetic step followed by an ion exchange step are within the scope of the invention. Preferably the salt has the formula $MX_a$ wherein a depends on the charge on the anion and the cation. This would be understood by the person skilled in the art.

In some preferred embodiments X is a monovalent anion and the metal is present as a divalent cation and the salt is of formula $MX_2$. The salt may be used in hydrated form.

The method involves admixture of the salt $MX_a$, ligand L and acid A. These may be admixed in the presence or absence of a solvent, with or without heating. A number of methods of synthesising the materials are possible and some of these are described in the examples.

The method may involve dissolving the metal salt and the acid in a first solvent, suitably a polar, preferably a polar protic solvent (eg methanol); and dissolving the ligand in a second solvent, suitably an organic solvent, suitably an aromatic solvent, preferably an aromatic halogenated solvent (eg dicholorobenzene).

The first and second solvents are suitably miscible but with different densities to allow slow diffusion between the two phases. This may be referred to herein as a solvent layering method.

The method may involve mixing a solution of the metal salt and the acid in a first solvent, suitably a polar, preferably a polar protic solvent (eg methanol); and a solution of the ligand in a second solvent, suitably an organic solvent, suitably an aromatic solvent (eg dicholorobenzene) with agitation eg stirring. After agitating the mixture for a sufficient period (eg 24 hours), the resultant powder (for example a nanopowder) may be collected by filtration. This may be referred to herein as a direct mixing method.

A similar method may involve heating a solution of the metal salt and the acid in a first solvent, suitably a polar, preferably a polar protic solvent (eg methanol), suitably to a temperature of 60 to 100° C., for example around 80° C.; and slowly adding a solution of the ligand in a second solvent, suitably an organic solvent, suitably an aromatic solvent (eg dicholorobenzene). Addition may be carried out over a period of, for example, 24 hours. The resultant powder may be collected by filtration. This may be referred to herein as a solvothermal reaction.

A further method may involve dry mixing the salt, the ligand and the acid, suitably with grinding, for example in a pestle and mortar. The mixture may then be heated in an oven, suitably for up to an hour, for example for about 15 min, at a temperature of 70 to 100° C., for example around 85° C. This may be referred to herein as a mechanosynthesis method.

According to a third aspect of the present invention there is provided a material of formula $[M(L)_{1.5}(A)^+]X^-G_n$ wherein M is a metal ion; L is a nitrogen-containing bidentate ligand; A is an anion of mandelic acid or a related acid; $X^-$ is an organic anion; G is a guest molecule; and n is from 0 to 5.

M, L, A and $X^-$ are preferably as defined in relation to the first aspect and preferred features of the second aspect are as defined in relation to the first aspect.

G is a guest molecule.

n is from 0 to 5. When n is 0 there are no guest molecules hosted in the porous chiral material. In such embodiments the material of the third aspect is the same as the material of the first aspect. When n is from 1 to 5 there are between 1 and 5 guest molecules accommodated in each unit cell of the porous organic material. When n is between 0 and 1 a fraction of the unit cells within the porous chiral material are occupied by a guest molecule. Thus some unit cells contain a guest molecule and some are empty; or a guest molecule may be positioned between unit cells.

In some embodiments the porous chiral material may host more than different type of guest molecule. It may also host solvent molecules.

According to a fourth aspect of the present invention there is provided a method of preparing a material of formula $[M(L)_{1.5}A]^+X^-G$, the method comprising contacting a material of formula $[M(L)_{1.5}X]^+A^-$ with a composition comprising a guest molecule G.

Preferred features of the fourth aspect are as defined in relation to the third aspect. Further preferred features of the third and fourth aspects of the invention will now be described.

Typically in the method of the fourth aspect the porous chiral material of formula $[M(L)_{1.5}X]^+A^-$ is immersed in a composition comprising the guest molecule. Typically the porous chiral material is immersed in the composition comprising the guest molecule for a period sufficient to allow an equilibrium to be reached.

The guest molecule may be provided neat (either enantiopure or as a mixture of enantiomers if chiral) or it may be dissolved in a solvent in which it is soluble but in which the porous chiral material is not. Suitable solvents will depend on the nature of the guest molecule.

Typically the solvent is an organic solvent, preferably a volatile organic solvent, for example dichloromethane. The solvent may enter the pores of the porous chiral material but it suitably does not bind as well as the guest molecule.

In some embodiments the composition comprising the guest molecule may contain impurities. These suitably do not bind to the porous chiral materials and thus the porous chiral materials of the invention may be used to purify the guest compound.

A wide range of different types of guest molecule may be hosted in the porous chiral materials of the present invention. The guest molecule may be a salt or an ion. Preferably it is a neutral species.

Preferably the guest molecule is a small organic molecule having less than 30 carbon atoms, suitably less than 25 carbon atoms, for example less than 20 carbon atoms.

The guest molecule may be aromatic or aliphatic in nature. It may be an unfunctionalised molecule or it may include one or more functional groups. For example it may include one or more of an alkene, an aldehyde, an alkyne, a ketone, a hydroxy group, a sulphide, a halide (especially chloro or bromo), an epoxide or a nitrile functionality.

In some embodiments the guest molecule may be a halogenated compound.

Examples of halogenated compounds that may be hosted by the chiral porous material include dichloromethane, alkyl chloride, 1-bromopropane, 1-bromoheptane, 1-bromononane, 1-bromododecane and 1,2-dichlorobenzene.

In some embodiments the guest molecule may be an alcohol.

Examples of hydroxy containing compounds that may be hosted by the porous chiral material of the invention include 2-propanol, allyl alcohol, linalool, citronellol, and 1-decen-3-ol.

In some embodiments the guest molecule may include unsaturation. Examples of compounds containing unsaturation that may be hosted by the porous chiral materials of the present invention include carbon disulphide, acetonitrile, toluene, 1, 2-dichlorobenzene, allyl alcohol, allyl chloride, linalool, citral, citronellol and 1-decen-3-ol.

In some embodiments the guest molecule may be a simple alkane.

Examples of alkanes that may be hosted by the chiral porous material of the present invention include hexane and cyclohexane.

In some embodiments the guest molecule includes an aromatic moiety.

In some embodiments the guest molecule is an alkyl phenol wherein the alkyl group has 2 to 6 carbon atoms and includes one or more functional groups. Suitably the functional group(s) is/are selected from alcohol, epoxide, alkene and nitrile.

In some embodiments the guest molecule G is a compound of formula (III):

wherein Ar is an aryl group and each of $R^1$ and $R^2$ is independently selected from hydrogen, hydroxide, nitrile, amino, halo, or an optionally substituted alkyl, alkenyl, alkynl, aryl or alkoxy group.

In embodiments in which $R^1$ is not hydrogen and $R^1$ and $R^2$ are different there is a stereocentre at position a. In such embodiments there is preferably an excess of one enantiomer accommodated in the host molecule.

Preferably at least 60% of the guest molecules are of the same enantiomer, preferably at least 70%, more preferably at least 80%, suitably at least 90%, for example at least 95%. Such a high degree of selectivity is observed even when the composition contacted with the material comprises a racemic mixture of the guest molecule G or when the other enantiomer is present in excess. Thus the chiral porous materials of the present invention exhibit enantioselectivity which enables determination of the structure of the most preferred enantiomers.

Ar is an aryl group.

Preferably Ar is an optionally substituted phenyl group. Suitable substituents include hydroxy, nitrile, amino, halo, alkoxy, mercapto, fluoro, carboxy and nitro.

Preferably Ar is an unsubstituted phenyl group.

Each of $R^1$ and $R^2$ is independently selected from hydrogen, hydroxide, nitrile, amino, halo or an oxygen substituted alkyl, alkenyl, aryl or alkoxy group.

Preferably $R^1$ is selected from hydrogen, hydroxide and nitrile.

In some embodiments $R^1$ is hydrogen. In some embodiments $R^1$ is hydroxyl.

In some embodiments $R^1$ is nitrile.

In some embodiments where $R^1$ is hydrogen, $R^2$ is preferably a group of formula $CHR^3R^4$ the guest molecule is a compound of formula (IV):

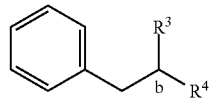
(IV)

When $R^3$ and $R^4$ are different, there is a stereogenic centre at the carbon designated b in figure (IV).

In some embodiments $R^3$ is hydroxy and $R^4$ is an alkyl group. Preferably $R^4$ is an alkyl group having 1 to 4 carbon atoms, more preferably 1 or 2 carbon atoms.

In embodiments in which are $R^1$ is a hydroxy, $R^2$ is preferably selected from an alkyl or alkenyl group. Preferably $R^1$ is selected from an alkyl or alkenyl group having 1 to 6, preferably 1 to 4 carbon atoms.

Suitably when $R^1$ is a hydroxy, $R^2$ is selected from methyl, ethyl, $CH=CH_2$ n-propyl, n-butyl and cyclopropyl.

In embodiments in which $R^1$ is nitrile, $R^2$ is preferably alkyl, more preferably $C_1$ to $C_4$ alkyl, preferably $C_1$ or $C_2$ alkyl.

Suitable guest compounds that may be hosted in the porous chiral materials of the present invention include the following:

a
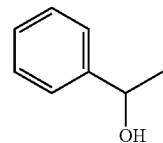

b
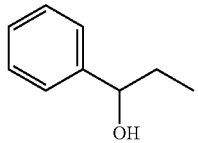

c
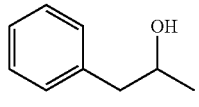

d
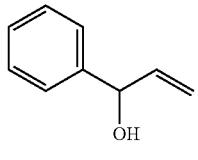

e
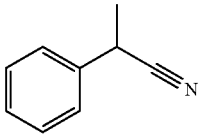

f
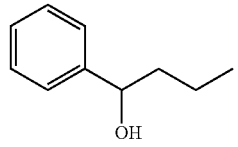

-continued g
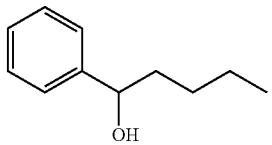

h
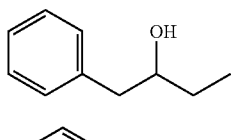

i
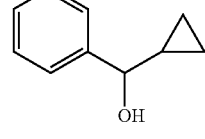

j
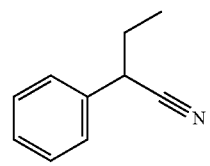

Advantageously the porous chiral materials of the present invention are able to bind chiral guest compounds within their structure. The resultant material incorporated in the host compound is suitably also crystalline and forms part of the overall crystal structure.

Such a crystal structure can then be determined by crystallographic techniques enabling the absolute stereochemistry of the guest compound to be determined within the larger structure of the host porous chiral material.

This means that even very small quantities of the guest material can be characterised by crystallography.

This is a significant advantage since traditional crystallisation methods require a minimum amount of material and for new compounds, trial and error is often used to determine the best crystallisation conditions, necessitating significant amounts of material.

The present invention thus allows trace amounts of material to be crystallised and the absolute stereochemistry thereof to be determined.

It will also be appreciated that the crystal structure of guest molecules which are not chiral may also be determined using the porous materials of the present invention.

The invention thus offers significant benefits in the fields of extraction of chemical compounds from natural products and identification of new chemical entities produced during pharmaceutical research.

The porous chiral material of the present invention may act as a chiral crystalline sponge. Thus according to a fifth aspect of the present invention there is provided the use of a porous chiral material of formula $[M(L)_{1.5}(A)]^+X^-$ as a crystalline sponge.

It has been found that chiral porous materials of the present invention when contacted with a mixture of enantiomers may preferentially bind one enantiomer over another. Thus the chiral porous material of the present invention may be used in a resolution method.

The invention may provide a method of separating enantiomers, the method comprising contacting a composition comprising a mixture of enantiomers with a material of the first aspect. After the mixture of enantiomers had been left for a period sufficient to achieve equilibrium the porous chiral material could be separated, suitable by removing the solid material from the composition containing the mixture of enantiomers. One enantiomer would be carried within the porous chiral material acting as a crystalline sponge and the other would remain in the composition in the reaction vessel.

Advantageously the porous chiral materials of the present invention may reversibly bind guest molecules. This enables the guest molecule to be released following characterisation which may be important in resolution methods or when very small levels of new chemical entities or natural products are involved. This also allows the host material to be reused to help determine the structure of further compounds.

The porous chiral materials of the present invention offer a number of significant advantages over porous materials of the prior art. The materials typically have adaptable pore sizes enabling them to accommodate different guest molecules.

In addition they are stable to solvent exchange, heat and humidity. Because of these features the chiral porous materials of the present invention not only find utility as chiral crystalline sponges but are also very useful as chiral stationary phases in chromatography columns.

According to a sixth aspect of the present invention there is provided a chromatography column comprising as a stationary phase a chiral porous material of formula $[M(L)_{1.5}(A)]^+X^-$ wherein M is a metal ion; L is a nitrogen-containing bidentate ligand; A is an anion of mandelic acid or a related acid; and $X^-$ is an anion.

Preferred features of the sixth aspect are as defined in relation to the first, second, third, fourth and fifth aspect.

Chromatography columns are known to those skilled in the art and comprise a tube in which the inside surface is coated with a material that acts as a stationary phase. The chromatography column of the present invention comprises a chiral porous material of formula $[M(L)_{1.5}(A)]^+X^-$ as a stationary phase but other features are typically as found in chromatography columns of the prior art.

The chromatography column of the sixth aspect may be a gas chromatography column or a liquid chromatography column. Preferably it is a gas chromatography column. The dimensions of the column will depend on the scale of purification for which it is intended top be used.

Suitably the stationary phase of the chromatography column of the sixth aspect comprises a chiral porous material of formula $[M(L)_{1.5}(A)]^+X^-$ coated onto a silica support, or an alternative support, e.g. a metal capillary.

The chromatography columns of the present invention have been found to be highly effective at separating enantiomers.

According to a seventh aspect of the present invention there is provided a method of separating a mixture of enantiomers, the method comprising passing a composition comprising the mixture of enantiomers through a chromatography column comprising as a stationary phase a chiral porous material of formula $[M(L)_{1.5}(A)]^+X^-$ wherein M is a metal ion; L is a nitrogen-containing bidentate ligand; A is an anion of mandelic acid or a related acid; and $X^-$ is an anion.

According to an eighth aspect of the present invention there is provided the use of a chiral porous material of formula $[M(L)_{1.5}(A)]^+X^-$ as a stationary phase in a chromatography column to separate enantiomers.

Preferred features of the seventh and eighth aspects are as defined in relation to the first, second, third, fourth, fifth and sixth aspects.

A particular benefit of the chiral porous materials of the present invention is that they are able to act as both a chiral stationary phase in a chromatography column and as a crystalline sponge which selectively binds one enantiomer.

It has been advantageously found that the chiral porous materials of the invention when used as crystalline sponges selectively bind the enantiomer having the longest retention time when the material is used as a stationary phase. Thus the material may be used to not only separate but also to identify enantiomers. This can be achieved without needing to provide an enantiopure reference material thus offering significant advantages over the prior art.

Thus the present invention may provide a method of separating and identifying an enantiomer from a composition comprising a mixture of enantiomers, the method comprising:

(a) passing a composition comprising the mixture of enantiomers through a chromatography column comprising as a stationary phase a chiral porous material of formula $[M(L)_{1.5}(A)]^+X^-$;

(b) contacting the composition comprising the mixture of enantiomers with a crystalline chiral porous material of formula $[M(L)_{1.5}(A)]^+X^-$ for a period sufficient for the composition to equilibrate; and (c) obtaining the crystal structure of the material obtained in step (b).

From the crystal structure of the material obtained in step (c) it is possible to identify the enantiomer having the longest retention time.

The chiral porous material can be used to separate enantiomers for a wide range of materials having different structures. They can be used to separate racemic mixtures or to separate compositions where one enantiomer is present in excess. They are especially useful at separating enantiomers having structures described herein in relation to the guest molecule G.

In particular the porous chiral materials of the present invention are useful for the separation of mixtures of enantiomers of compounds having the structures of formula (III).

Suitably the porous chiral materials of the present invention are useful for the separation of mixtures of enantiomers of (a) 1-phenylethanol, (b) 1-phenyl-1-propanol, (c) 1-phenyl-2-propanol, (d) α-vinylbenzyl alcohol, (e) 2-phenylpropanenitrile, (f) 1-phenyl-1-butanol, (g) 1-phenyl-1-pentanol, (h) 1-phenyl-2-butanol, (i) α-cyclopropylbenzyl alcohol, and (j) 2-phenylbutyronitrile.

The invention will now be further defined with reference to the following non-limiting examples.

EXAMPLES

All reagents and solvents were commercially available and used as received.

Instrumentation

Powder X-Ray diffraction was performed on a PANalytical X'Pert MPD Pro using Cu Kα (λ=1.5418 Å) radiation with a 1D X'Celerator strip detector. Single crystal data were collected on a Bruker Quest PHOTON 100 CMOS system equipped with a Cu Kα INCOATEC Imus microfocus source (A=1.5418 Å, T=100(2) K). Thermogravimetric analysis was performed using a TA Instruments TGA-Q50 at a constant rate of 5° C./min from 25° C. to 550° C. SEM images were taken by Hitachi SU-70 and JEOL JSM-7500F systems with high resolution. Gas chromatographic measurements were performed on a GC-14B (Shimadzu, Japan) system with flame ionization detector. Nitrogen (99.999%) was used as the carrier gas. A β-DEX 225 capillary column (30 m long×0.25 mm i.d.×0.25 μm film thickness, Supelco Inc.), a Chirasil L-Val capillary column (25 m long×0.25 mm i.d.×0.12 µm film thickness, Agilent Technologies), and a Cyclosil-B capillary column (30 m long×0.32 mm i.d.×0.25 µm film thickness, Agilent Technologies) were employed as commercial columns for comparison.

X-Ray Structure Analysis

This was carried out using standard techniques known to those skilled in the art. In all cases indexing was performed using APEX2 Data integration and reduction were performed using SaintPlus 6.01 as provided by Bruker. Absorption correction was performed by multi-scan method implemented in SADABS. Space groups were determined using XPREP implemented in APEX2. Structures were solved using Patterson Method (SHELXS-97), expanded using Fourier methods and refined on $F^2$ using nonlinear least-squares techniques with SHELXL-97 contained in APEX2, WinGX v1.70.01 and OLEX2 v1.2.6 programs packages. All non-H framework atoms as well as ordered guest molecules and anions were refined anisotropically and without restraints or constraints. Atoms of disordered guest molecules have been found from difference Fourier map and were initially refined freely, however due to overlap of disordered parts the restraints have been used to impose feasible geometry on molecules. The targeted distances have been taken from CSD Database.

Example 1—Synthesis of [Co(biyp)$_{1.5}$(1S)]$^+$OTf$^-$ (Material A)

Material A may be prepared by four different methods, as follows:

(i) Solvent Layering

A 5 mL methanol solution of 0.4 mmol Co(CF$_3$SO$_3$)$_2$.6H$_2$O (180 mg) and 0.4 mmol of enantiopure (S)-mandelic acid (1S, 60.8 mg) was layered above a 5 mL 1,2-dichlorobenzene (DCB) solution of 0.6 mmol 4,4'-bipyridine (bipy, 93.6 mg). The amount of bipy can be varied from 0.3-0.6 mmol (46.8-93.6 mg). A buffer solution of 5 mL 1:1 methanol/DCB was layered between the top and the bottom layers to allow for slow diffusion over 7 days. Red rectangular prismatic crystals were harvested and exchanged with dichloromethane (DCM) daily for 5 days to remove DCB. The resultant crystalline samples were stored in neat DCM prior to use in further experiments.

The crystal structure of [Co(biyp)$_{1.5}$(1S)]$^+$OTf$^-$ is shown in FIG. 1.

(ii) Direct Mixing 0.8 mmol Co(CF$_3$SO$_3$)$_2$.6H$_2$O (360 mg) and 0.8 mmol of enantiopure (S)-mandelic acid (1S, 121.6 mg) was stirred in a 5 mL of methanol. A solution of 1.2 mmol bipy (187.2 mg) in 5 mL DCB was added to and stirred over one day. The amount of bipy can be varied from 0.6-1.2 mmol (93.6-187.2 mg). The pink nanocrystalline powder thereby obtained was filtered and washed with DCM (20 mL) 10 times. The resultant material was stored in neat DCM prior to use in further experiments.

(iii) Solvothermal Reaction

A solution of 0.8 mmol Co(CF$_3$SO$_3$)$_2$.6H$_2$O (360 mg) and 0.8 mmol of enantiopure (S)-mandelic acid (1S, 121.6 mg) was stirred in 5 mL methanol at 80° C. 1.2 mmol bipy (187.2 mg) dissolved in 5 mL DCB at 80° C. was added over one day with continuous stirring. The amount of bipy can be varied 0.6-1.2 mmol (93.6-187.2 mg). The pink powder thereby obtained was filtered and washed with DCM (20 mL) 10 times. The resultant material was stored in neat DCM prior to use in further experiments.

(iv) Mechanosynthesis 0.4 mmol Co(CF$_3$SO$_3$)$_2$.6H$_2$O (180 mg) and 0.4 mmol enantiopure (S)-mandelic acid (1S, 60.8 mg) was ground in a mortar and pestle for 1 min. 0.6 mmol bipy (93.6 mg) was then placed in the mortar along with 20 µL of DCB. The mixture was further ground for 1 minute and then transferred to an 85° C. oven for 15 min. The resultant powder was washed with DCM (10 mL) 5 times and stored in neat DCM prior to use in further experiments.

Example 2—Fabrication of Capillary Column Coated with Material A

Fused silica capillary (30 m long×0.32 mm i.d., Yongnian Optic Fiber Plant, Hebei, China) was pretreated according to the following recipe before dynamic coating: the capillary was washed with 1 M NaOH for 2 h, ultrapure water for 30 min, 0.1 M HCl for 2 h, and ultrapure water until the outflow reached pH 7.0.

The capillary was then dried with N$_2$ at 100° C. overnight. Material A was coated onto the pre-treated capillary column via a dynamic coating method. 3 mL DCM suspension of material A (1 mg/mL) was first filled into the capillary column under gas pressure, and then pushed through the column at a constant N$_2$ pressure of 20 KPa to leave a wet coating layer on the inner wall of the capillary column. After coating, the capillary column was settled for 2 h for conditioning under N$_2$. Further conditioning of the capillary column was carried out using a temperature program: 30° C. for 10 min, ramp from 30° C. to 150° C. at a rate of 3° C. min$^{-1}$, and 150° C. for 2 h.

Example 3—Inclusion of Racemates and Other Guest Molecules in Single Crystals of Material A Multiple single crystals of [Co(byp)$_{1.35}$(1S)]$^+$OFT$^-$ were submerged in excess amounts of neat racemates and other guest molecules at ambient temperature for a time sufficient to reach equilibrium, typically believed to be about 5 days from previous experiments. By placing multiple crystals in parallel, it increases the probability of selecting high quality crystal for SCXRD examination.

Example 4—Microgram Scale Inclusion of Geraniol and Nerol in Material A

Figure 7:
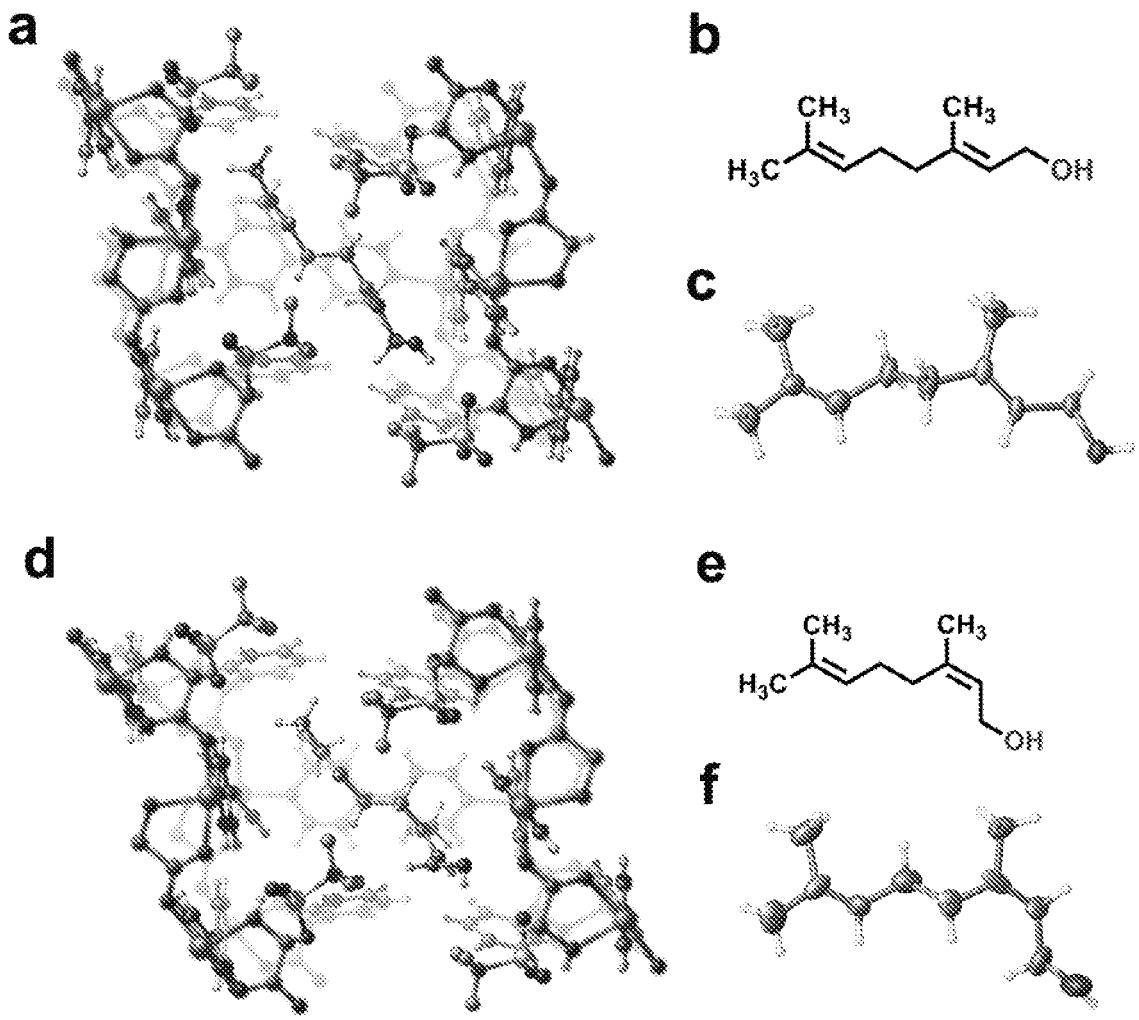
FIG. 7 shows the binding sites of geraniol and nerol in Material A of the invention.

A 20 uL DCM solution of 17 mg geraniol or nerol was added to a 0.3 mL Qsertvial™ low adsorption vial. A single crystal of material A was placed at the bottom of the vial and submerged in the solvent. Then the vial was loosely capped to allow DCM evaporation over 2 days. The crystal was coated in immersion oil for transfer and mounting. The inventors were able to determine the crystal structures of these compounds for the first time. FIG. 7 shows the binding sites of geraniol (a) and nerol (d) in Material A. Structural formulae (b, e) and molecular structures (c, 0 of geraniol and nerol, respectively. Thermal ellipsoids are drawn at the 50% probability level.

Example 5—Stability Test

Figure 8:
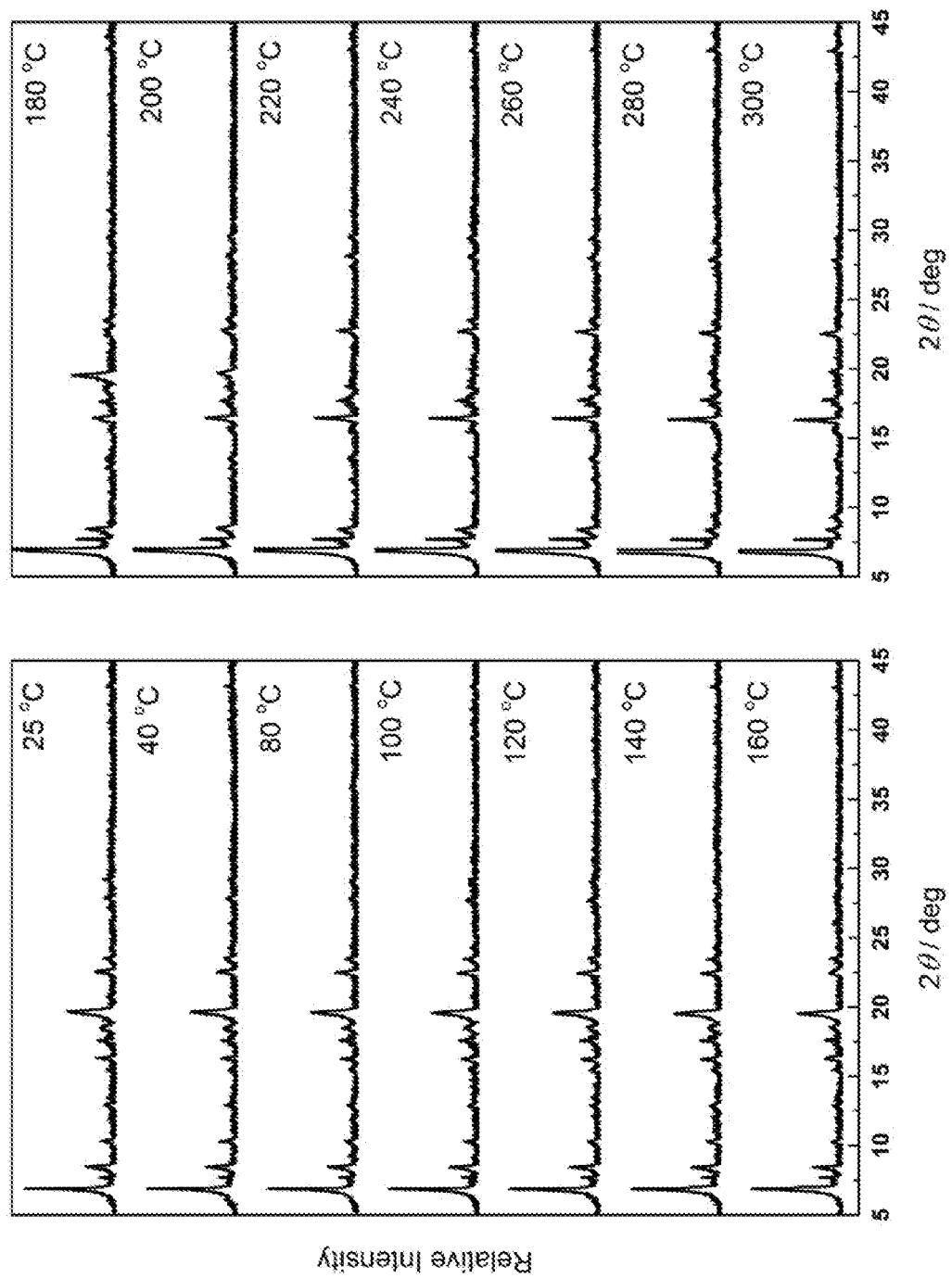
FIG. 8 shows stability data for Material A.

The crystalline sample of desolvated material A was exposed to 40° C. and 75% relative humidity for 7 days in a desiccator. The condition was achieved by using a super-saturated aqueous solution of NaCl maintained at 40° C. After 7 days, the samples were removed from the desiccator and characterized by PXRD. The results showed that material A remained stable under these humidity conditions. The heat stability of the material A was tested by heating the material progressively to 300° C. Powder X-ray diffraction patterns were taken at various temperatures as the material was heated. The results shown in FIG. 8 demonstrate that the crystal structure of the material did not change following heating to 300° C.

Example 6—Synthesis of Other Materials

The following further materials were prepared as follows:

[Co(bipy)$_{1.5}$(2R)][OTf] (Material B)

Figure 2:
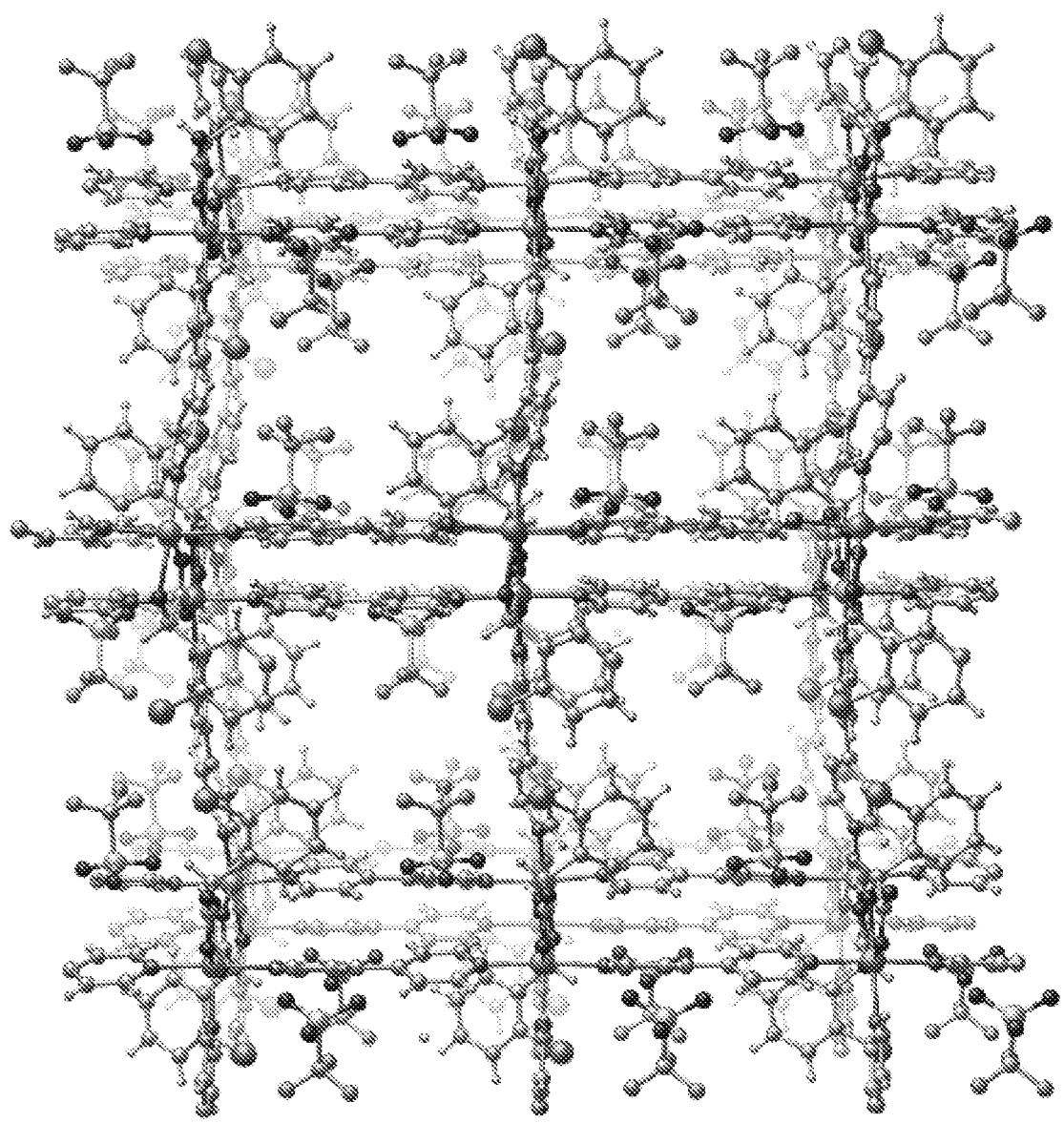
FIG. 2 shows the crystal structure of [Co(bipy)$_{1.5}$(2R)][OTf].DCB.

The same procedure as that used to prepare compound A was followed with the exception that (R)-2-chloromandelic acid (0.40 mmol, 740 mg, 2R) was used instead of (S)-mandelic acid (1S). Red rectangular prismatic crystals were obtained in ~75% yield. A view of the crystal structure of [Co(bipy)$_{1.5}$(2R)][OTf].DCB is presented in FIG. 2. Guest molecules are omitted for clarity.

[Co(bipy)$_{1.5}$(3R)][OTf] (Material C)

Figure 3:
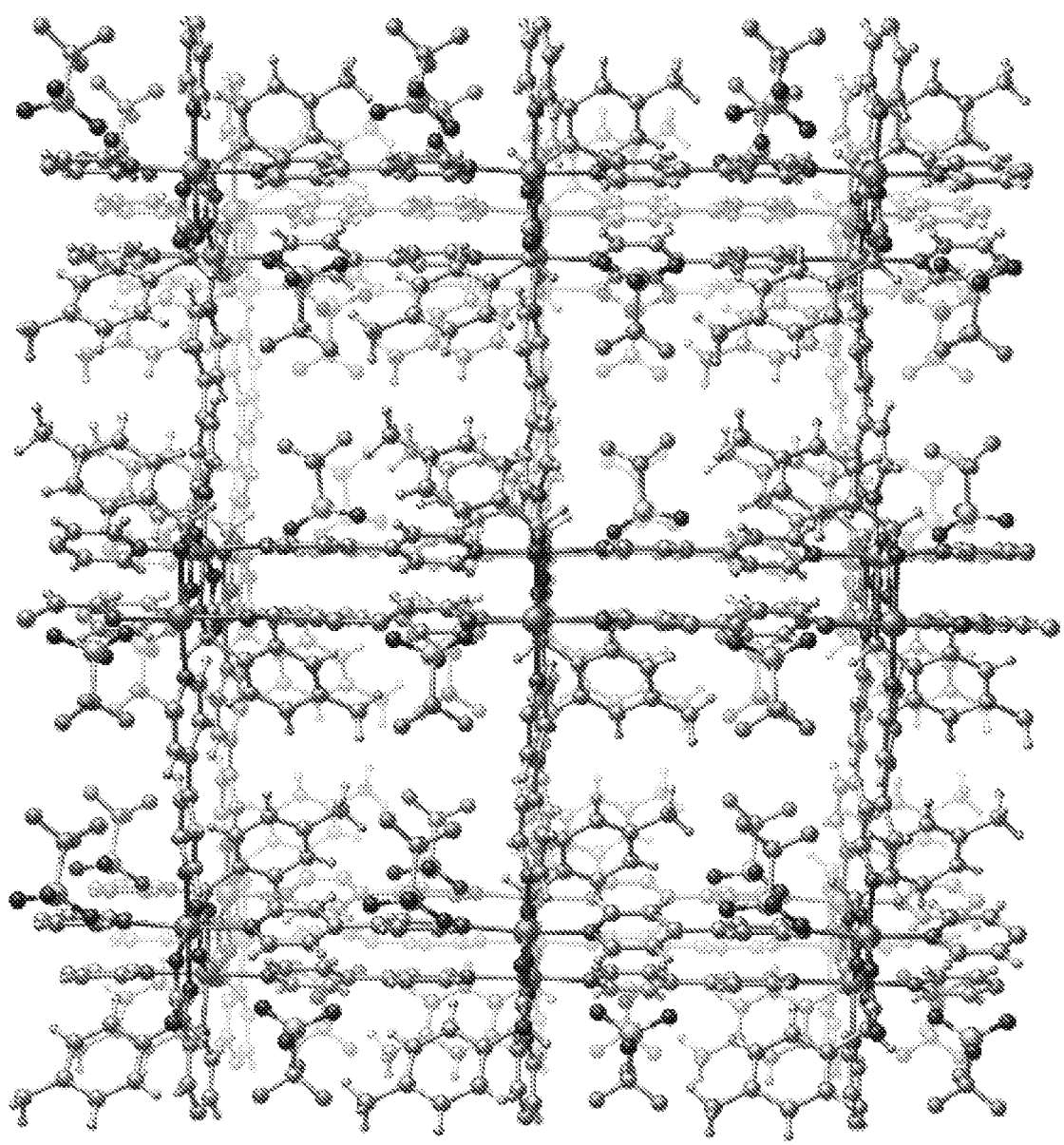
FIG. 3 shows the crystal structure of [Zn(bipy)$_{1.5}$(3R)][OTf].BTF.

The same procedure as that used to prepare compound A was following with the exception that (R)-3-chloromandelic acid (0.40 mmol, 740 mg, 3R) was used instead of (S)-mandelic acid (1S) and benzotrifluoride (BTF) was instead of DCB. Red rectangular prismatic crystals were obtained in ~75% yield. The crystals aggregate as clusters which are not suitable for study by single crystal X-ray crystallography. The Zn(II) analogue, [Zn(bipy)$_{1.5}$(1S)][OTf].BTF, was synthesized by using Zn(OTf)$_2$.6H$_2$O (150 mg). A view of the crystal structure of [Zn(bipy)$_{1.5}$(3R)][OTf].BTF is presented in FIG. 3. Guest molecules are omitted for clarity.

[Co(bipy)$_{1.5}$(4R)][OTf] (Material D)

Figure 4:
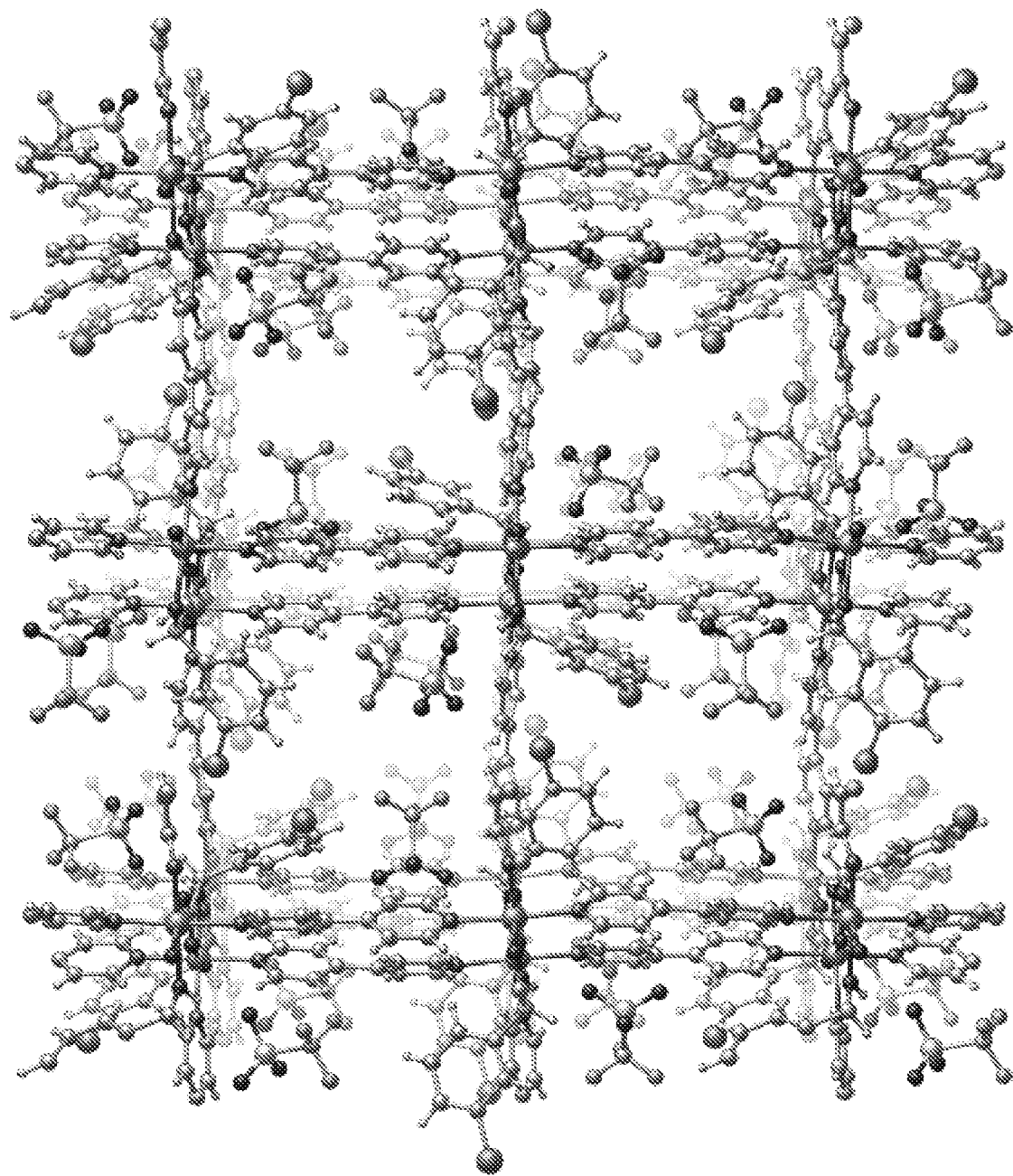
FIG. 4 shows the crystal structure of [Co(bipy)$_{1.5}$(4R)][OTf].BTF.

The same procedure as that used to prepare compound A was followed with the exception that (R)-3-chloromandelic acid (0.40 mmol, 740 mg, 4R) was used instead of (S)-mandelic acid (1S) and benzotrifluoride (BTF) was used instead of DCB, was followed. Red rectangular prismatic crystals were obtained in ~75% yield. A view of the crystal structure of [Co(bipy)$_{1.5}$(4R)][OTf].BTF is presented in FIG. 4. Guest molecules are omitted for clarity.

[Co(bipy)$_{1.5}$(13R)][OTf].BTF (Material E)

Figure 5:
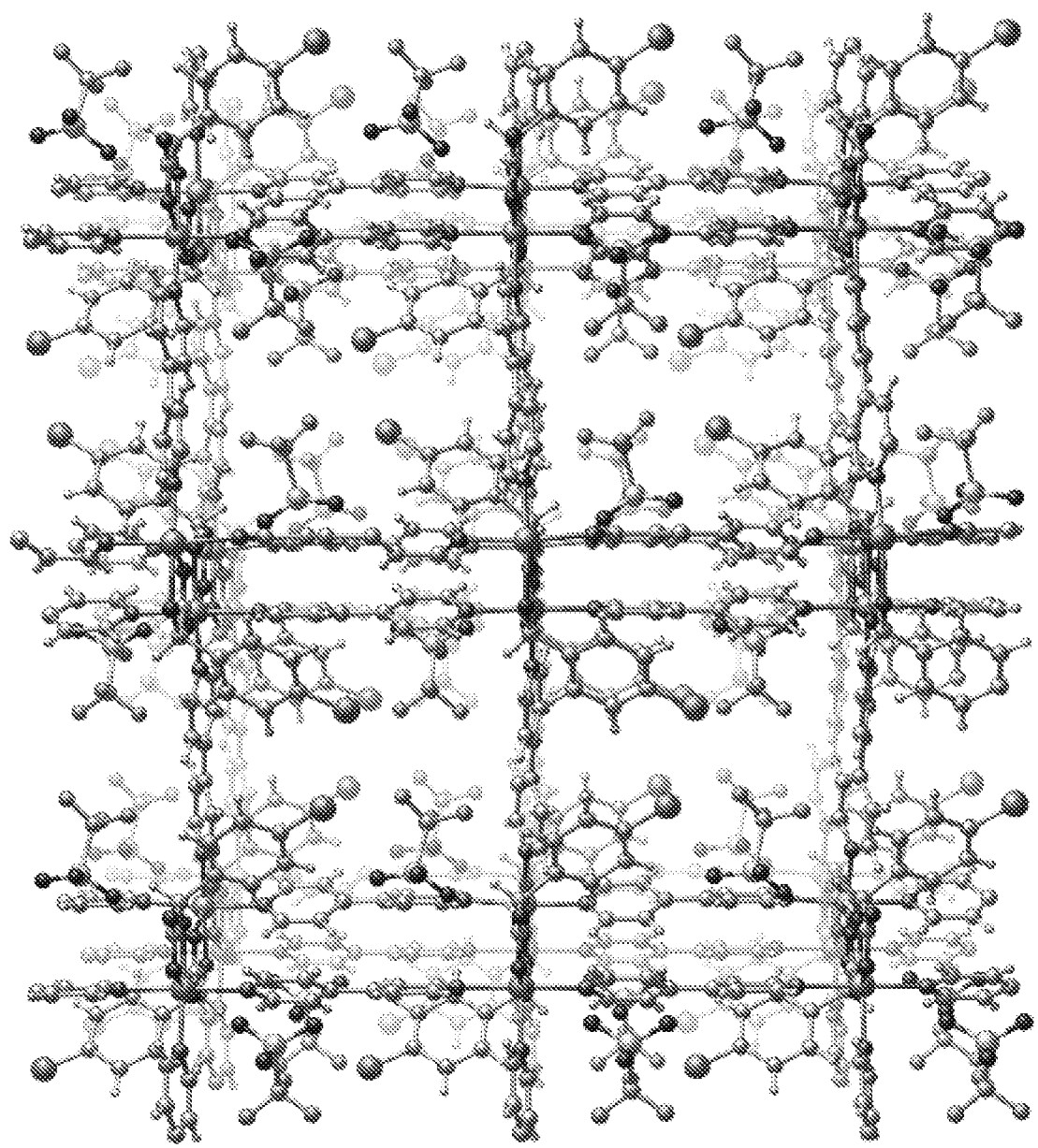
FIG. 5 shows the crystal structure of [Co(bipy)$_{1.5}$(13R)][OTf].BTF.

The same procedure as that used to prepare material A was followed with the exception that (R)-4-methylmandelic acid (0.4 mmol, 660 mg, 13R) was used instead of (S)-mandelic acid (1S) and benzotrifluoride (BTF) was used instead of DCB, was followed. Red rectangular prismatic crystals were obtained in ~75% yield. A view of the crystal structure of [Co(bipy)$_{1.5}$(13R)][OTf].BTF is presented in FIG. 5. Guest molecules are omitted for clarity.

[Co(LB)$_{1.5}$(1S)][OTf] (Material F)

Material F was prepared by the following solvent layering method: A solution of 0.4 mmol Co(CF$_3$SO$_3$)$_2$.6H$_2$O (180 mg) and 0.4 mmol of (S)-mandelic acid (1S, 60.8 mg) in 5 ml of methanol was layered above a buffer solution which had in turn been layered above a solution of 0.6 mmol 1,2-bis(4-pyridyl)ethane (LB, 110.4 mg) in 5 mL 1,2-dichlorobenzene (DCB). The amount of LB can vary from 0.3-0.6 mmol (55.2-110.4 mg). The buffer solution was 5 mL of 1:1 methanol/DCB. These solvent layers were allowed to diffuse over 7 days, at which point red rectangular prismatic crystals had formed. These crystals were harvested and exchanged with dichloromethane (DCM) daily for 5 days to remove DCB. The resultant crystalline samples were stored in DCM prior to further use.

Figure 6:
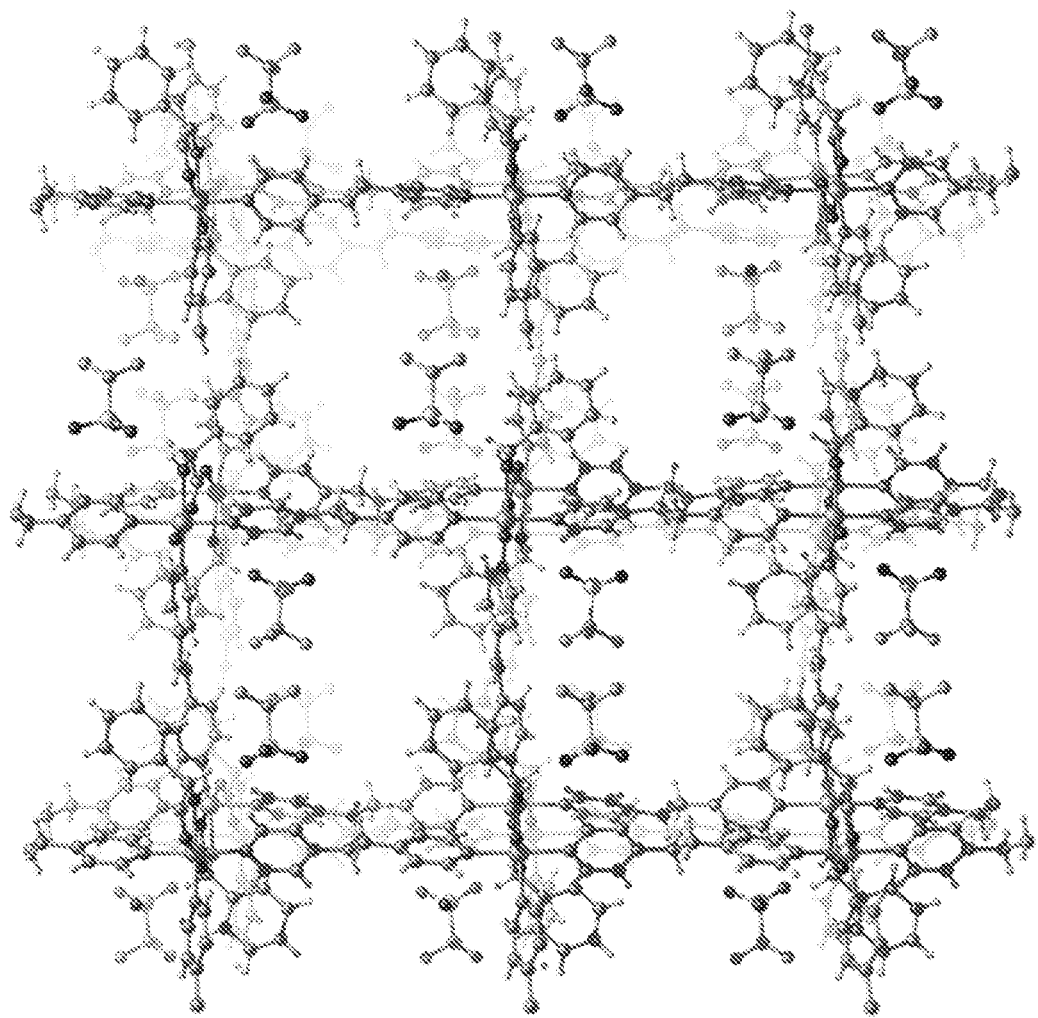
FIG. 6 shows the crystal structure of [Co(LB)$_{1.5}$(1S)][OTf].DCM.

The crystal structure of [Co(LB)$_{1.5}$(1S)][OTf].DCM is shown in FIG. 6. Guest molecules are omitted for clarity.

Crystallographic parameters for materials A to F are given in table 1:

TABLE 1

| | [Co(bipy)$_{1.5}$(1S)][OTf]•DCB | [Co(bipy)$_{1.5}$(2R)][OTf]•DCB | [Zn(bipy)$_{1.5}$(3R)][OTf]•BTF | [Co(bipy)$_{1.5}$(4R)][OTf]•BTF |
|---|---|---|---|---|
| formula | C$_{59.42}$H$_{45.61}$Cl$_{3.81}$Co$_2$F$_6$N$_6$O$_{12}$S$_2$ | C$_{58.8}$H$_{43.2}$Cl$_6$CO$_2$F$_6$N$_6$O$_{12}$S$_2$ | C$_{55.8}$H$_{40}$Cl$_2$F$_9$N$_6$O$_{12.8}$S$_2$Zn$_2$ | C$_{57}$H$_{49}$Cl$_2$Co$_2$F$_9$N$_6$O$_{14}$S$_2$ |
| fw | 1466.48 | 1534.47 | 1436.10 | 1465.90 |
| T (K) | 100(2) | 100(2) | 100(2) | 100(2) |
| cryst system | Monoclinic | Monoclinic | Orthorhombic | Monoclinic |
| space group | P2$_1$ | P2$_1$ | P2$_1$2$_1$2$_1$ | P2$_1$ |
| a (Å) | 10.3499(5) | 10.3260(5) | 10.2977(4) | 10.1623(4) |
| b (Å) | 25.4610(12) | 25.5247(11) | 22.9238(9) | 25.6092(11) |
| c (Å) | 11.4211(6) | 11.4411(5) | 25.5012(10) | 11.4729(5) |
| β (°) | 91.403(3) | 91.155(2) | 90 | 90.244(3) |
| V (Å$^3$) | 3008.8(3) | 3014.9(2) | 6019.9(4) | 2985.8(2) |
| Z | 2 | 2 | 4 | 2 |
| Dc (g·cm$^{-3}$)$^a$ | 1.308 | 1.382 | 1.386 | 1.394 |
| μ (mm$^{-1}$) | 7.281 | 8.171 | 3.286 | 6.709 |
| F (000) | 1490.0 | 1552.0 | 2905.0 | 1492.0 |
| R$_{int}$ | 0.0584 | 0.0523 | 0.0637 | 0.0746 |
| GOF | 1.045 | 1.118 | 1.101 | 1.054 |
| R$_1$ (I > 2σ(I)) | 0.0509 | 0.0815 | 0.0689 | 0.0659 |
| wR$_2$ (all data) | 0.1159 | 0.1875 | 0.2031 | 0.1456 |
| Δρ$_{max}$ (e Å$^{-3}$) | 0.77 | 0.84 | 2.38 | 0.52 |
| Δρ$_{min}$ (eÅ$^{-3}$) | −0.64 | −0.76 | −0.57 | −0.55 |
| Flack | 0.048(4) | 0.246(5) | 0.150(6) | 0.079(4) |

| | [Co(bipy)$_{1.5}$(13R)][OTf]•BTF | [Co(LB)$_{1.5}$(1S)][OTf]•DCM |
|---|---|---|
| formula | C$_{59}$H$_{55}$Co$_2$F$_9$N$_6$O$_{14}$S$_2$ | C$_{57.27}$H$_{57.54}$Cl$_{6.55}$Co$_2$F$_6$N$_6$O$_{12.77}$S$_2$ |
| fw | 1425.07 | 1562.19 |
| T (K) | 100(2) | 100(2) |
| cryst system | Monoclinic | Monoclinic |
| space group | P2$_1$ | P21 |
| a (Å) | 10.1791(3) | 13.5720(4) |
| b (Å) | 25.6037(8) | 10.1658(3) |
| c (Å) | 11.4781(4) | 26.4276(8) |
| β (°) | 90.4539(18) | 103.3217(17) |
| V (Å$^3$) | 2991.36(17) | 3548.11(18) |
| Z | 2 | 2 |

| | | 1.347 | 1.189 |
|---|---|---|---|
| Dc (g·cm$^{-3}$)$^a$ | | 1.347 | 1.189 |
| μ (mm$^{-1}$) | | 5.874 | 7.140 |
| F (000) | | 1460.0 | 1593 |
| $R_{int}$ | | 0.0590 | 0.0739 |
| GOF | | 1.089 | 1.079 |
| $R_1$ (I > 2σ(I)) | | 0.0655 | 0.0906 |
| $wR_2$ (all data) | | 0.1511 | 0.2163 |
| $\Delta\rho_{max}$ (e Å$^{-3}$) | | 0.60 | 0.87 |
| $\Delta\rho_{min}$ (eÅ$^{-3}$) | | −0.53 | −0.86 |
| Flack | | 0.173(5) | 0.191(5) |

$^a$calculated for activated materials.

Example 7—Separation of Enantiomers

The gas chromatography column of example 2 was used to separate enantiomers of the following compounds: (a) 1-phenylethanol, (b) 1-phenyl-1-propanol, (c) 1-phenyl-2-propanol, (d) α-vinylbenzyl alcohol, (e) 2-phenylpropanenitrile, (f) 1-phenyl-1-butanol, (g) 1-phenyl-1-pentanol, (h) 1-phenyl-2-butanol, (i) α-cyclopropylbenzyl alcohol, and (j) 2-phenylbutyronitrile.

Figure 9:
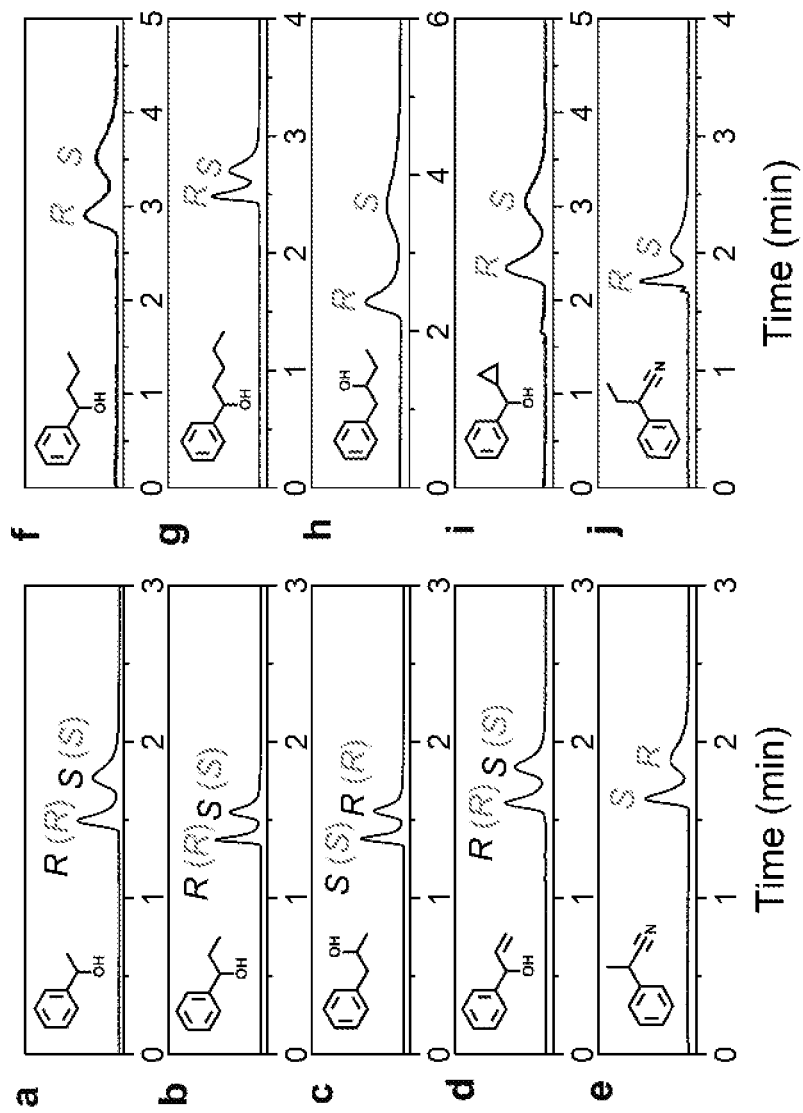
FIG. 9 shows chromatograms for the separation of enantiomers.

The chromatograms for the separation of these compounds is shown in FIG. 9.

The separation was found to be superior to that achieved for the same racemic mixtures using three different types of known commercial chiral columns (β-DEX 225, Cyclosil-B, and Chirasil L-Val). The comparative data is shown in table 2.

TABLE 2

| | Material A | | | | β-DEX 225 | | | | Cyclosil-B | | | | Chirasil L-Val | | | |
|---|---|---|---|---|---|---|---|---|---|---|---|---|---|---|---|---|
| No. | T$^a$ | P$^b$ | t$^c$ | R$^d$ | T$^a$ | P$^b$ | t$^c$ | R$^d$ | T$^a$ | P$^b$ | t$^c$ | R$^d$ | T$^a$ | P$^b$ | t$^c$ | R$^d$ |
| a | 130 | 150 | 2.1 | 1.5 | 130 | 150 | 5.5 | 1.5 | 130 | 150 | 6.5 | 1.5 | 80 | 100 | 9.0 | 1.1 |
| b | 150 | 150 | 1.7 | 1.5 | 120 | 150 | 9.7 | 1.5 | 150 | 150 | 4.6 | $^e$ | 100 | 125 | 6.0 | 1.1 |
| c | 150 | 150 | 1.7 | 1.5 | 110 | 150 | 13 | 1.7 | 130 | 150 | 7.2 | 1.5 | 150 | 150 | 1.7 | —$^e$ |
| d | 140 | 150 | 2.1 | 1.4 | 120 | 150 | 11 | 1.9 | 140 | 150 | 7.5 | 1.2 | 100 | 150 | 5.0 | 0.5 |
| e | 150 | 150 | 2.4 | 1.4 | 115 | 150 | 13 | 1.5 | 150 | 150 | 4.2 | 2.2 | 150 | 150 | 1.5 | —$^e$ |
| f | 135 | 100 | 4.0 | 1.5 | 110 | 150 | 20 | 1.6 | 110 | 150 | 30 | 1.3 | 135 | 150 | 4.5 | —$^e$ |
| g | 150 | 100 | 3.0 | 1.4 | 150 | 150 | 8.0 | —$^e$ | 150 | 100 | 13 | 1.7 | 100 | 150 | 12.0 | 0.8 |
| h | 130 | 150 | 5.0 | 1.5 | 150 | 150 | 6.0 | —$^e$ | 130 | 150 | 11 | 1.5 | 80 | 150 | 12.0 | 1 |
| i | 150 | 150 | 3.5 | 1.5 | 130 | 150 | 15 | 1.7 | 150 | 150 | 9.0 | —$^e$ | 100 | 150 | 12 | 0.3 |
| j | 150 | 150 | 2.5 | 1.4 | 120 | 150 | 14 | 0.4 | 150 | 150 | 5.4 | 2.2 | 150 | 150 | 2.0 | —$^e$ |

$^a$separation temperature (° C.),
$^b$N$_2$ pressure (KPa),
$^c$total separation time (min),
$^d$resolution,
$^e$cannot be separated.
All the separations were performed with optimized conditions.

Example 8

Figure 11:
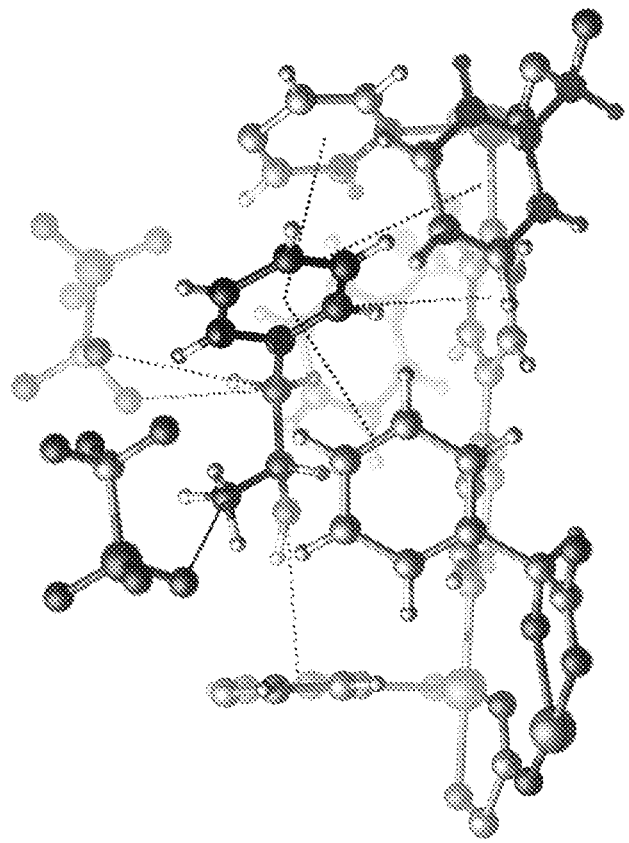
FIG. 11 shows the guest binding sites and absolute configuration of compound c.
Figure 10:
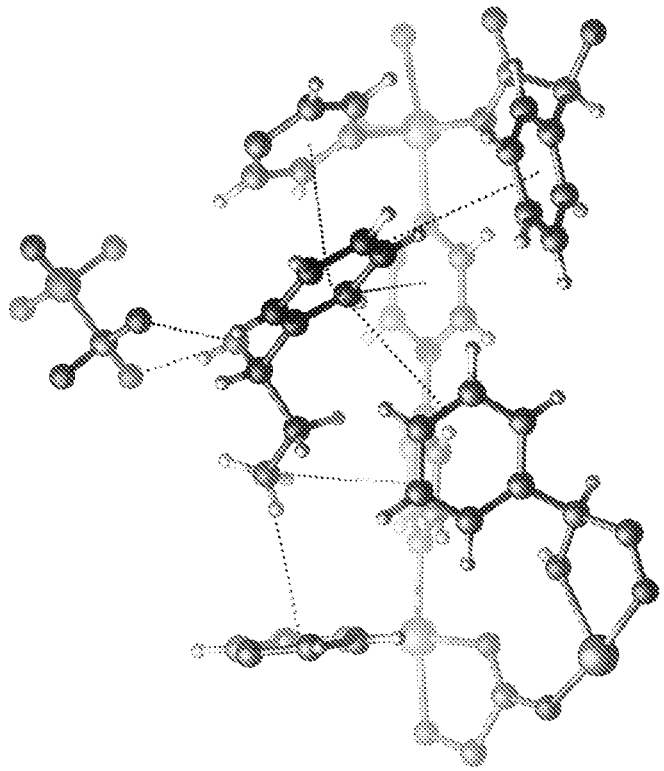
FIG. 10 shows the guest binding sites and absolute configuration of compound b.

In order to gain insight into the nature of the supramolecular interactions between the analytes and the pores of material A, the inventors isolated and studied by SCXRD the ten host-guest compounds formed after crystals of material A were exposed for 5 days to the racemates used in example 7. Existing CSPs (e.g., polysaccharides and cyclodextrins) are not amenable to diffraction studies so the precise nature of preferred binding sites in a CSP has not yet been directly observed. That material A has an extra-framework cation enables its cavities to adapt to the guest. When coupled with its low symmetry space group, this adaptability allowed the inventors to observe the binding sites of material A using in high resolution using a conventional x-ray diffractometer. The absolute configurations of the preferred chiral guest molecules were unambiguously determined and validated thanks to the anomalous scattering effects of heavy atoms (Co and S). The host-guest binding sites are resolved for all 10 racemates. The absolute configuration of the chiral analytes was found to correspond with the longest retention time as confirmed by using an enantiopure reference standard for all 10 examples. The guest binding sites and absolute configuration of compounds b and c are shown in FIG. 10 and FIG. 11 respectively.

Example 9

The ability of material A to act as a chiral crystalline sponge to facilitate crystallisation and structure determination was tested successfully for the following further guest molecules: Dichloromethane, carbon disulphide, acetonitrile, 2-propanol, hexane, cyclohexane, toluene, 1,2-dichlorobenzene, allyl alcohol, allyl chloride, 1-bromopropane, 1-bromoheptane, 1-bromononane, 1-bromododecane, linalool, citral, citronellol and 1-decen-3-ol.

The invention claimed is:

1. A porous chiral material of formula [M(L)$_{1.5}$(A)]$^+$X$^-$ wherein M is selected from a group consisting of: cobalt, chromium, iron, nickel, manganese, calcium, magnesium, cadmium, copper, and zinc; L is 4,4'-bipyridine or a two-connected nitrogen ligand having the formula (L2N):

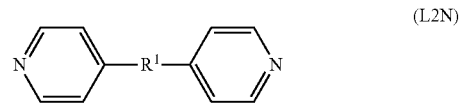

(L2N)

wherein $R^1$ is an optionally substituted linker group; A is an anion of formula (II):

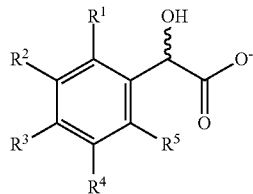

(II)

wherein the stereocentre may be (R) or (S) and $R^1$, $R^2$, $R^3$, $R^4$, and $R^5$ is each independently selected from hydrogen, hydroxy, amino, halo, alkyl, fluoroalkyl, sulfo, mercapto, alkoxy, nitro, acyl, and nitrilo, and $X^-$ comprises a sulfonate or carboxylate anion.

2. A porous chiral material according to claim 1 wherein L is selected from a group consisting of: 4,4'-bipyridine, 1,2-bis(4-pyridyl)ethane, and 4,4'-bipyridylacetylene.

3. A porous chiral material according to claim 1 wherein A is the anion of (S)-(−)-mandelic acid.

4. A material of formula $[M(L)_{1.5}(A)^+]X^-G_n$ wherein M is selected from a group consisting of: cobalt, chromium, iron, nickel, manganese, calcium, magnesium, cadmium, copper, and zinc; L is 4,4'-bipyridine or a two-connected nitrogen ligand having the formula (L2N):

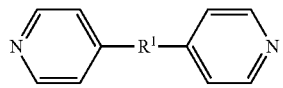

(L2N)

wherein $R^1$ is an optionally substituted linker group; A is an anion of formula (II):

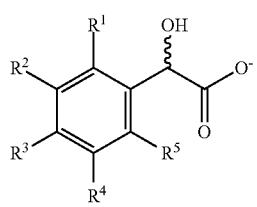

(II)

wherein the stereocentre may be (R) or (S) and $R^1$, $R^2$, $R^3$, $R^4$, and $R^5$ is each independently selected from hydrogen, hydroxy, amino, halo, alkyl, fluoroalkyl, sulfo, mercapto, alkoxy, nitro, acyl, and nitrilo, and $X^-$ comprises a sulfonate or carboxylate anion; G is a guest molecule; and n is from 0 to 5.

5. A crystalline sponge comprising a porous chiral material of formula $[M(L)_{1.5}(A)]^+X^-$, wherein wherein M is selected from a group consisting of: cobalt chromium iron nickel manganese, calcium, magnesium cadmium, copper, and zinc; L is 4,4'-bipyridine or a two-connected nitrogen ligand having the formula (L2N):

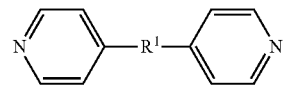

(L2N)

wherein $R^1$ is an optionally substituted linker group; A is an anion of formula (II):

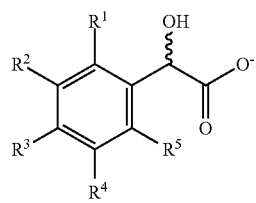

(II)

wherein the stereocentre may be (R) or (S) and $R^1$, $R^2$, $R^3$, $R^4$, and $R^5$ is each independently selected from hydrogen, hydroxy, amino, halo, alkyl, fluoroalkyl, sulfo, mercapto, alkoxy, nitro, acyl, and nitrilo, and $X^-$ comprises a sulfonate or carboxylate anion.

6. A method of separating enantiomers, the method comprising contacting a composition comprising a mixture of enantiomers with a porous chiral material of formula $[M(L)_{1.5}(A)]^+X^-$, wherein M is selected from a group consisting of: cobalt, chromium, iron, nickel, manganese, calcium, magnesium, cadmium, copper, and zinc; L is 4,4'-bipyridine or a two-connected nitrogen ligand having the formula (L2N):

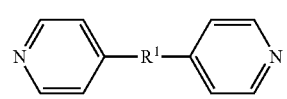

(L2N)

wherein $R^1$ is an optionally substituted linker group; A is an anion of formula (II):

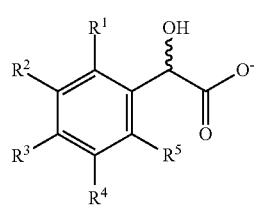

(II)

wherein the stereocentre may be (R) or (S) and $R^1$, $R^2$, $R^3$, $R^4$, and $R^5$ is each independently selected from hydrogen, hydroxy, amino, halo, alkyl, fluoroalkyl, sulfo, mercapto, alkoxy, nitro, acyl, and nitrilo, and X comprises a sulfonate or carboxylate anion.

7. A method of separating enantiomers according to claim 6, the method comprising passing a composition comprising the mixture of enantiomers through a chromatography column comprising as a stationary phase the porous chiral material of formula $[M(L)_{1.5}(A)]^+X^-$.

8. A method of separating enantiomers according to claim 7, the method comprising:

(a) passing a composition comprising the mixture of enantiomers through a chromatography column comprising as a stationary phase the porous porous material of formula $[M(L)_{1.5}(A)]^+X^-$;

(b) contacting the composition comprising the mixture of enantiomers with a crystalline chiral porous material of formula $[M(L)_{1.5}(A)]^+X^-$ for a period sufficient for the composition to equilibrate, wherein M is selected from a group consisting of: cobalt, chromium, iron, nickel, manganese, calcium, magnesium, cadmium, copper, and zinc; L is 4,4'-bipyridine or a two-connected nitrogen ligand having the formula (L2N):

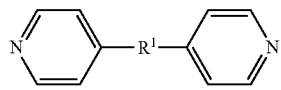

(L2N)

wherein $R^1$ is an optionally substituted linker group; A is an anion of formula (II):

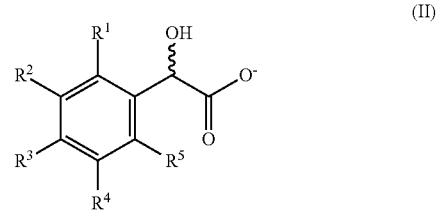

(II)

wherein the stereocentre may be (R) or (S) and $R^1$, $R^2$, $R^3$, $R^4$, and $R^5$ is each independently selected from hydrogen, hydroxy, amino, halo, alkyl, fluoroalkyl, sulfo, mercapto, alkoxy, nitro, acyl, and nitrilo, and $X^-$ comprises a sulfonate or carboxylate anion; and (c) obtaining the crystal structure of the material obtained in step (b), thereby identifying an enantiomer.

\* \* \* \* \*